(12) United States Patent
Pan

(10) Patent No.: US 9,758,484 B2
(45) Date of Patent: Sep. 12, 2017

(54) BASE ADDITION SALTS OF NITROXOLINE AND USES THEREOF

(71) Applicant: Asieris Pharmaceutical Technologies Co., Ltd., Taizhou, Jiangsu Province (CN)

(72) Inventor: Ke Pan, Chadds Ford, PA (US)

(73) Assignee: Asieris Pharmaceutical Technologies Co., Ltd., Jiangsu, China Medical Taizhou (CN)

( * ) Notice: Subject to any disclaimer, the term of this patent is extended or adjusted under 35 U.S.C. 154(b) by 0 days.

(21) Appl. No.: 14/777,185

(22) PCT Filed: Mar. 17, 2014

(86) PCT No.: PCT/US2014/030532
§ 371 (c)(1),
(2) Date: Sep. 15, 2015

(87) PCT Pub. No.: WO2014/145723
PCT Pub. Date: Sep. 18, 2014

(65) Prior Publication Data
US 2016/0031819 A1    Feb. 4, 2016

Related U.S. Application Data

(60) Provisional application No. 61/790,059, filed on Mar. 15, 2013.

(51) Int. Cl.
*C07D 215/38* (2006.01)
*C07D 215/24* (2006.01)
*A61K 9/00* (2006.01)

(52) U.S. Cl.
CPC .......... *C07D 215/38* (2013.01); *A61K 9/0019* (2013.01); *C07D 215/24* (2013.01)

(58) Field of Classification Search
CPC ... C07D 215/38; C07D 215/24; A61K 9/0019
See application file for complete search history.

(56) References Cited

U.S. PATENT DOCUMENTS

| | | | |
|---|---|---|---|
| 2,745,832 A * | 5/1956 | Fath | C07D 215/30 514/187 |
| 3,872,128 A | 3/1975 | Byck | |
| 4,329,185 A | 5/1982 | Dimov et al. | |
| 4,376,162 A | 3/1983 | Kawata et al. | |
| 8,729,097 B2 * | 5/2014 | Liu | A61K 31/47 514/312 |
| 2003/0105066 A1 | 6/2003 | Soldato et al. | |
| 2008/0207673 A1 | 8/2008 | Xilinas | |
| 2011/0301163 A1 | 12/2011 | Liu et al. | |

FOREIGN PATENT DOCUMENTS

| | | |
|---|---|---|
| JP | S 5768831 A | 4/1982 |
| JP | S 57101835 A | 6/1982 |
| JP | H 03284734 A | 12/1991 |
| JP | 2003520814 A | 7/2003 |
| JP | 2010500875 A | 1/2010 |
| JP | 2010070557 A | 4/2010 |
| JP | 2012100678 A | 5/2012 |
| WO | 9116820 A1 | 11/1991 |
| WO | 0154691 A1 | 8/2001 |
| WO | 2005/063711 A1 | 7/2005 |
| WO | 2005/063722 * | 7/2005 |
| WO | 2006119987 A2 | 11/2006 |
| WO | 2008022759 A2 | 2/2008 |
| WO | 2010/136105 A2 | 12/2010 |
| WO | 2011091973 A1 | 8/2011 |

OTHER PUBLICATIONS

Pelletier, Antimicrobial agents and chemotheropy, vol. 39(3), 707-713, 1995.*
Chang, Oncotarget, vol. 6(37), 39806-39820, 2015.*
International Search Report/Written Opinion issued Aug. 7, 2014 in PCT/US2014/030532.
Pelletier. Antimicrobial Agents and Chemotherapy 39(3); 707-713, 1995.
PubChem, Compound Summary for: CID 70976725; creation date: Mar. 21, 2013; retrieved: Jul. 15, 2014.
Office Action issued Feb. 12, 2016 in AU Application No. 2014232722.
Serajuddin, A. T. M., "Salt formation to improve drug solubility," Advanced Drug Delivery Reviews, vol. 59, pp. 303-616 (2007) (Abstract only).
CAS Registry No. 1038989-83-1; STN Entry Date Aug. 6, 2008.
Office Action issued Aug. 23, 2016 in CA Application No. 2907338.
Supplemental Search Report issued Jul. 15, 2016 in EP Application No. 14762230.2.
Stahl, "Preparation of Water-Soluble Compounds Through Salt Formation", The Practice of Medical Chemistry, pp. 601-615 (Jan. 2003).
Thai et al., "Arene Ruthenium Oxinato Complexes: Synthesis, Molecular Structure and Catalytic Activity for the Hydrogenation of Carbon Dioxide in Aqueous Solution", Journ. Organ Chem., vol. 694, 3973-3981 (2009).
CAPLUS AN2007:1329600 ("Theoretical Study on the Effects of Substituting Group on the Electronic Spectrum of 8-hydroxyquinoline Lithium", Gongneng Cailiao, vol. 38, No. 5, 1 pg. (2007)).
Klofutar et al., "Thermodynamics of Deprotonation and Dissociation Steps of 8-hydroxyquinoline, 5-chloro-8-hydroxyquinoline and 5-nitro-8-hydroxyquinoline in Aqueous Media", Spectro Acta, vol. 31A, pp. 1093-1097 (1975).
Extended European Search Report issued Nov. 3, 2016 in EP Application No. 14762230.2.
Georgieva et al., "Possibilities for Imparting Stable Antimicrobial Properties to Polyester Textile Materials", Man-Made Textiles in India Research Assoc., vol. 50, No. 11, pp. 392-394 (2007).

(Continued)

*Primary Examiner* — D M Seaman
(74) *Attorney, Agent, or Firm* — Panitch Schwarze Belisario & Nadel LLP

(57) ABSTRACT

Novel base addition salts of nitroxoline with improved solubility and increased urine secretion under physiological conditions are described. Pharmaceutical compositions and methods of treatment using the pharmaceutical compositions are also described.

20 Claims, 8 Drawing Sheets

(56) References Cited

OTHER PUBLICATIONS

PubChem, Compound Summary for: CID 488236; creation date: Aug. 1, 2005; retrieved: Sep. 30, 2016.
Office Action issued Nov. 15, 2016 in JP Application No. 2016-503414.
Manolova et al., "Ultraviolet and H-NMR Studies on the Products of the Chemical Modification of a,w-Dichloropoly (Oxyethylene) with Potassium 5-Nitro-8-Quinolinolate", Eur. Polym. Journ., vol. 29, No. 5, pp. 715-720 (1993).
Georgieva et al., "Possibilities for Creating Cellulose Textile Materials with Antimicrobial and Haemostatic Properties", Man-Made Textile in India, vol. 48, pp. 216-219 (2005).
Office Action issued Nov. 16, 2016 in KR Application No. 10-2015-7028976.
Bastin et al., "Salt Selection and Optimisation Procedures for Pharmaceutical New Chemical Entities", Organic Process Research Develop., vol. 4, No. 5, pp. 427-435 (2000).
Office Action dated Jun. 6, 2017 in JP Application No. 2016-503414.

* cited by examiner

BASE ADDITION SALTS OF NITROXOLINE AND USES THEREOF

FIELD OF THE INVENTION

The present invention relates to novel base addition salts of nitroxoline having improved solubility and stability in aqueous solutions as compared to nitroxoline or other salts of nitroxoline. The present invention also relates to pharmaceutical compositions comprising the base addition salts of nitroxoline, and methods of treating or preventing diseases, disorders, and conditions using these pharmaceutical compositions.

BACKGROUND OF THE INVENTION

Nitroxoline is an antimicrobial agent which has been commercially marketed for a long time for the treatment of urinary tract infections. It was recently discovered that nitroxoline is also active in inhibiting angiogenesis [1] and inhibiting the growth and invasion of cancer [2, 3].

Nitroxoline is orally administered to patients. Pharmacokinetic studies in humans indicated that nitroxoline can be rapidly absorbed into the blood for circulation [4]. Nitroxoline has a very short half-life ($t_{1/2}$) in humans, with the $t_{1/2}$=2.63 hour. Thus, nitroxoline is quickly metabolized and excreted, mainly through urine. Therefore, to maintain continuous drug exposure, nitroxoline drug products are usually prescribed at three times a day (TID) or four times a day (QID).

Nitroxoline also has low solubility in water. Therefore, it is typically prepared in immediate-release formulations, which allows for the release of nitroxoline in gastric liquids in the stomach, and subsequent absorption in the intestine. Although the crystal structure of a hydrochloride (HCl) addition salt of nitroxoline has been reported by Yatsenko et al. [5], no solubility data of any nitroxiline salts, including the nitroxoline HCl salt, have been disclosed. Due to the low water solubility of nitroxoline, no controlled release formulations of nitroxoline or injectable formulations of nitroxiline have been reported or developed for human uses to date.

Novel salts of nitroxoline with improved water solubility would provide for the development of optimized drug formulations of nitroxoline, which would allow patients to be administered such nitroxoline drugs formulations with less frequency, thereby improving the compliance of drug administration. Drug dosing compliance is critical to warrant the drug's adequate exposure and bioavailability in patients, and hence its efficacy in treating diseases. A steadier drug level in the blood stream delivered by an optimized formulation may also reduce adverse effects. An improved solubility in water would further enable the preparation of nitroxoline salts in liquid compositions.

Novel salts of nitroxoline with improved stability would also provide for the development of optimized drug formulations and improve the manufacturing process. Nitroxoline sublimes at high temperatures [6], which causes several problems in the process of manufacturing. For example, sublimed nitroxoline causes contamination during the drying process by accumulating on the surfaces of the manufacturing place and equipment. Thus, when manufactured into tablets, for example, nitroxoline may penetrate the coating films and contaminate the containers.

Accordingly, there exists a need in the art for novel salts of nitroxoline that have improved water solubility and improved stability as compared to nitroxoline.

BRIEF SUMMARY OF THE INVENTION

The present invention satisfies these needs by providing novel base addition salts of nitroxoline. Base addition salts of nitroxoline according to the invention have improved solubility in water and other aqueous media, and improved stability as compared to nitroxoline, and can thus be formulated into improved pharmaceutical compositions.

In one general aspect, the present invention provides base addition salts of nitroxoline. The base addition salts are preferably alkali metal salts, amine salts, or ammonium salts.

In another general aspect, the present invention provides a method of preparing a base addition salt of nitroxoline comprising mixing nitroxoline and a base in a solvent to obtain the base addition salt of nitroxoline, and recovering the base addition salt of nitroxoline from the solvent.

In yet another general aspect, the present invention provides a crystal of nitroxoline choline salt, wherein the crystal has peaks at the diffraction angles (2θ) with an exactness of ±0.2θ: 9.96, 12.12, 17.72, and 20.08 in its powder X-ray diffraction pattern.

And in yet another general aspect, the present invention relates to pharmaceutical compositions comprising a therapeutically effective amount of a base addition salt of nitroxoline and a pharmaceutically acceptable carrier.

Other aspects of the present invention include methods of treating or preventing diseases, disorders, or conditions in a subject in need thereof, comprising administering to the subject a composition comprising a therapeutically effective amount of a base addition salt of nitroxoline according to the invention. Diseases, disorders, and conditions to be treated or prevented are those for which nitroxoline is known to effective against, e.g., urinary tract infections; a disease associated with angiogenesis, such as tumor or cancer; and dementia or Alzheimer's disease.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
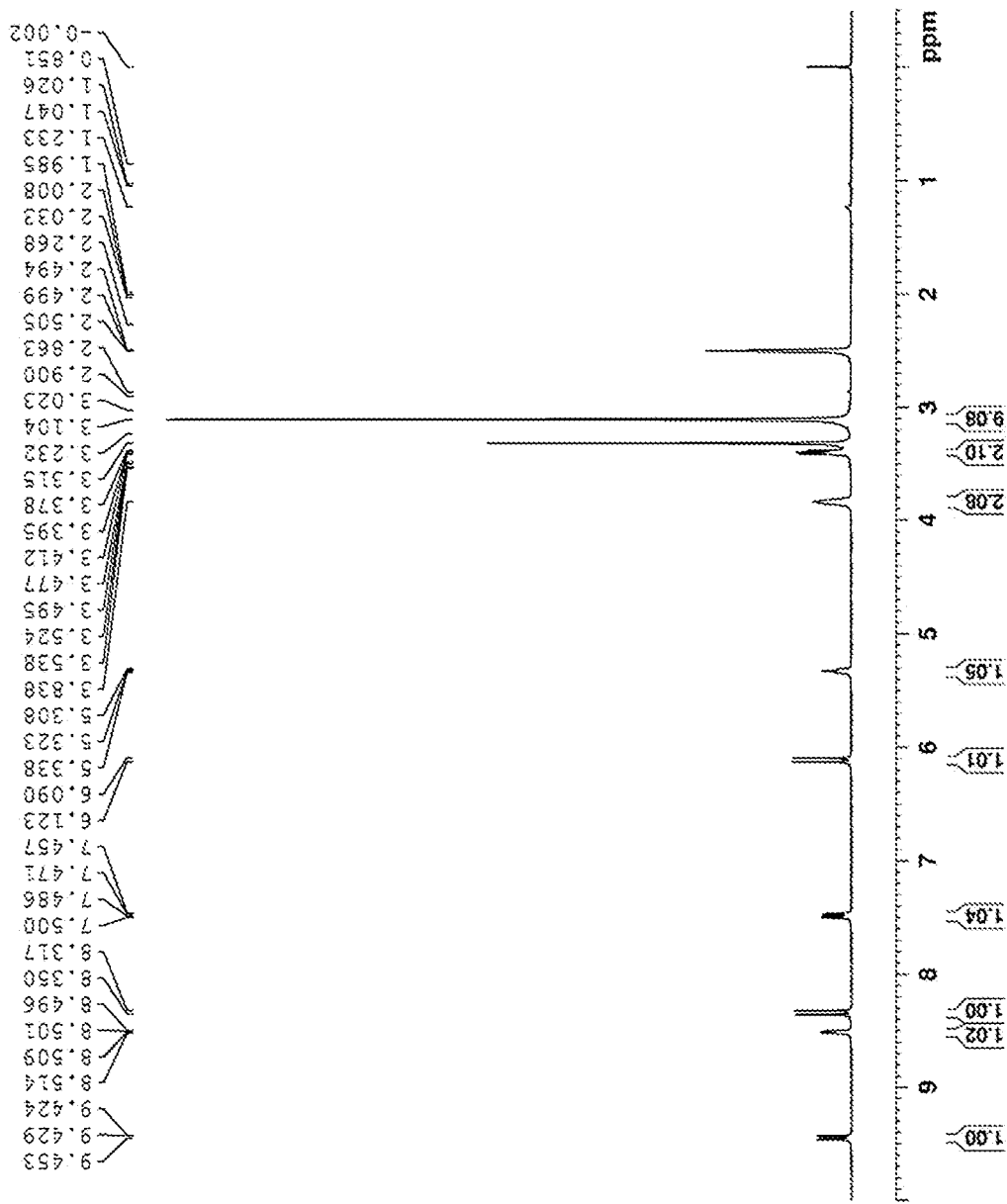
FIG. 1 provides the $^1$H-NMR spectrum of nitroxoline choline salt.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the term "aliphatic" or "aliphatic group" refers to a saturated or unsaturated linear (i.e., straight chain) or branched hydrocarbon group, and non-aromatic rings (i.e., alicyclic). Aliphatics can be saturated, meaning that the carbon atoms are joined together by single binds (alkanes or cycloalkanes) or unsaturated, meaning that the carbon atoms are joined together by double bonds (alkenes or cycloalkenes) or triple bonds (alkynes or cycloalkynes). Aliphatic groups encompass alkyl, alkenyl, alkynyl, and alicyclic groups.

Unless otherwise noted, the term "alkyl" as used herein means a saturated, unbranched or branched hydrocarbon chain containing at least one carbon atom. Examples of alkyls include, but are not limited to, methyl, ethyl, propyl, butyl, pentyl, hexyl, heptyl, octyl, nonyl, isopropyl, isobutyl, 2-methylpentyl, 3-methylpentyl, 2,2,-dimethylbutyl, 2,3-dimethylbutyl, 2-methylhexly, 2,3-dimethylhexyl, 2,2,-dimethylhexyl, and 3,3-dimethylhexyl. An alkyl group can be unsubstituted or substituted with one or more suitable substituents.

Unless otherwise noted, the term "alkenyl" as used herein means an unsaturated, unbranched or branched hydrocarbon chain having one or more carbon-carbon double bonds. Examples of alkenyls include, but are not limited to, ethenyl, propenyl, butenyl, pentenyl, hexenyl, 2-methyl-2-pentenyl, and 2-ethyl-2-hexenyl. An alkenyl group can be unsubstituted or substituted with one or more suitable substituents.

Unless otherwise noted, the term "alkynyl" as used herein means an unsaturated, unbranched or branched hydrocarbon chain having one or more carbon-carbon triple bonds. Examples of alkynyls include, but are not limited ethynyl, propynyl, butynyl, pentynyl, hexynyl, and 3-methyl-1-butynyl.

Unless otherwise noted, the term "alkoxy" denotes an organic unit having the general formula —OR, wherein R is an aliphatic (i.e., alkyl, alkenyl, alkynyl, alicyclic). An alkoxy group can be, for example, methoxy and ethoxy. Other examples of alkoxy groups include, but are not limited to, propoxy, isopropoxy, isobutoxy, and tert-butoxy.

Unless otherwise noted, the terms "alicyclic" refers to a non-aromatic cyclic hydrocarbon ring having at least three carbon atoms. Preferably, an alicyclic group has three to twelve carbon atoms, more preferably three to eight carbon atoms in the ring structure, and most preferably five to six carbon atoms in the ring structure. An alicyclic group can be saturated (cycloalkane), or unsaturated, meaning that at least two carbon atoms are joined together by a double bond (cycloalkene) or triple bond (cycloalkyne). An alicyclic group can be substituted or unsubstituted with one or more suitable substituents.

As used herein, the terms "heterocyclic" and "heterocyclic ring" refer to an alicyclic group, i.e., saturated or unsaturated cyclic hydrocarbon ring having at least three carbon atoms, wherein one or more carbon atoms of the cyclic hydrocarbon ring is substituted with a heteroatom, such as oxygen, nitrogen, or sulfur. Preferably, a heterocyclic ring has three to twelve carbon atoms in the ring position with at least one of the carbon atoms being substituted for a heteroatom, and more preferably five to six carbon atoms with one to two of the carbon atoms in the ring being substituted with a heteroatom. A heterocyclic ring can be unsubstituted or substituted with one or more suitable substituents.

As used herein "aryl" refers to an aromatic monocyclic or polycyclic hydrocarbon group having at least five carbon atoms in the ring position. Examples of aryl groups include, but are not limited to, phenyl and naphthalenyl. An aryl group can be unsubstituted or substituted with one or more suitable substituents, and said substitution can be at any position on the ring.

As used herein "heteroaryl" and "heteroaryl ring" refer to a monocyclic or polycyclic aromatic ring system having at least five carbon atoms in the ring position, wherein one or more of the carbon atoms are substituted for a heteroatom, such as nitrogen, oxygen, and sulfur. Preferably, a heteroaryl ring has five to twelve carbon atoms in the ring position with at least one of the carbon atoms being substituted for a heteroatom, and more preferably five to six carbon atoms with one to three, and more preferably one to two, of the carbon atoms in the ring being substituted with a heteroatom. A heterocyclic ring can be unsubstituted or substituted with one or more suitable substituents. Examples of heteroaryl rings include, but are not limited to, imidazolyl, pyrimidinyl, tetrazolyl, thienyl, pyridyl, pyrrolyl, pyrazolyl, oxazolyl, triazolyl, and benzofuryl.

As used herein, "amine" has its ordinary meaning as known to one skilled in the art and broadly refers to a compound containing a nitrogen atom with a lone pair. The term "amine" is intended to encompass aliphatic amines (including alkylamines, alenylamines, alkynylamines, and alicyclic amines), heterocyclic amines, arylamines, heteroaryl amines, polyamines, basic amino acids, and amino sugars. Preferred aliphatic amines include alkylamines Amines can be substituted with one or more suitable substituents.

As used herein the term "alkylamine" refers to an amine, wherein the nitrogen atom is substituted with one or more alkyl groups, such as methyl or ethyl. An alkylamine can be a primary amine, meaning that the amine is substituted with one alkyl group; a secondary amine, meaning that that amine is substituted with two alkyl groups; or a tertiary amine, meaning that the amine is substituted with three alkyl groups. The alkyl groups of a secondary or tertiary amine can be the same or different. As illustrative and nonlimiting examples, an alkylamine can be dimethylamine (secondary amine having a nitrogen atom substituted with two methyl groups), methylethylamine (secondary amine having a nitrogen atom substituted with a methyl group and an ethyl group), or triethylamine (a tertiary amine having a nitrogen atom substituted with three ethyl groups).

An alkylamine can be unsubstituted or substituted with one or more suitable substituents. A substituted alkylamine means that the one or more alkyl groups of the alkylamine are substituted with one or more suitable substituents.

As used herein, the term "alkenylamine" refers to an amine, wherein the nitrogen atom is substituted with one or more alkenyl groups, such as ethenyl or propenyl. An alkenylamine can be a primary amine, secondary amine, or tertiary amine The alkenyl groups of a secondary or tertiary alkenyl amine can be the same or different. An alkenylamine can be unsubstituted or substituted with one or more suitable substituents. As illustrative and nonlimiting example, an alkenylamine can be methyldiallylamine As used herein, the term "alkynylamine" refers to an amine, wherein the nitrogen atom is substituted with one or more alkynyl groups, such as ethynyl or propynyl. An alkynylamine can be a primary amine, secondary amine, or tertiary amine The alkynyl groups of a secondary or tertiary alkynyl amine can be the same or different. An alkynylamine can be unsubstituted or substituted with one or more suitable substituents. As illustrative and nonlimiting examples, an alkynylamine can N-methyl-di(2-propynyl)amine or 2-propyne-1-amine.

As used herein, the term "heterocyclic amine" refers to a heterocyclic ring, wherein at least one carbon atom of the hydrocarbon ring is substituted with a nitrogen atom. Preferably a heterocyclic amine has one to two carbon atoms of the hydrocarbon ring substituted with nitrogen atoms. A heterocyclic amine can be unsubstituted or substituted with one or more suitable substituents at any position of the heterocyclic ring, including the one or more nitrogen atoms. In addition to having at least one carbon atom of the hydrocarbon ring substituted with a nitrogen atom, a heterocyclic amine can also have one or more carbon atoms substituted with other heteroatoms, such as oxygen and sulfur. Examples of heterocyclic amines include, but are not limited to, piperazine, pyrrolidine, and morpholine.

As used herein, "arylamine" refers to an amine, wherein the nitrogen atom is substituted with one or more aryl groups, such as phenyl. The nitrogen atom of an arylamine can be substituted with one, two, or three aryl groups. The term arylamine is intended to encompass amines, wherein the nitrogen atom is substituted with at least one aryl group, and optionally one or more aliphatic groups, such as alkyl groups. An arylamine can be unsubstituted or substituted with one or more suitable substituents. A substituted arylamine means that the one or more aryl groups of the arylamine, and in certain embodiments the one or more alicyclic, e.g., alkyl, groups are substituted with one or more suitable substituents. As illustrative and nonlimiting examples, an arylamine can be aniline, N-methylaniline, 4-methylaniline, and 4-hydroxylaniline.

As used herein, "heteroaryl amine" refers to a heteroaryl ring, wherein at least one carbon atom of the aromatic ring system is substituted with a nitrogen atom. Preferably, a heteroaryl amine has one to three carbon atoms of the aromatic ring substituted with nitrogen atoms, and more preferably one to two carbon atoms substituted with nitrogen atoms. A heteroaryl amine can be unsubstituted or substituted with one or more suitable substituents at any position of the heteroaryl ring. In addition to having at least one carbon atom of the hydrocarbon ring substituted with a nitrogen atom, a heteroaryl amine can also have one or more carbon atoms substituted with other heteroatoms, such as oxygen and sulfur. Examples of heteroaryl amines include, but are not limited to pyridine, pyrrole, pyrimidine, imidazole, quinazoline, purine, pyrazole, and triazole.

As used herein, "alicyclic amine" refers to an amine, wherein the nitrogen atom is substituted with one or more alicyclic groups, such as cyclohexyl. The nitrogen atom of an alicyclic amine can be substituted with one, two, or three alicyclic groups. The term alicyclic amine is also intended to encompass amines, wherein the nitrogen atom is substituted with at least one alicyclic group and at least other aliphatic group, such as an alkyl group. An alicyclic amine can be unsubstituted or substituted with one or more suitable substituents. A substituted alicyclic amine means that the one or more alicyclic groups, or alkyl groups, of the alicyclic amine are substituted with one or more suitable substituents. As illustrative and nonlimiting examples, an alicyclic amine can be cyclohexylamine, cyclopentylamine, N-methylcyclohexylamine, and 4-methylcyclohexylamine As used herein, the term "polyamine" refers to a non-cyclic amine having more than one nitrogen atom containing a lone pair. The term "polyamine" is intended to encompass "diamines." As used herein, a "diamine" is a polyamine having two nitrogen atoms containing a lone pair. Polyamines can be substituted with one or more suitable substituents. Examples of polyamines, including diamines, include, but are not limited to, ethylenediamine, 1,3-diaminopropane, hexamethylenediamine, spermidine, and spermine An amino acid is an organic acid having one or more than one alkaline radical such as amino, guanidino, imino, or hydrazine radical attached at any carbon atom other than carbon one. Amino acids can be naturally or nonaturally occurring. Most naturally occurring amino acids are "L-form" amino acids, however a few are "D-form" amino acids. As used herein, the term "basic amino acid" refers to an amino acid having an additional alkaline radical that can act as a base, i.e., can accept a proton. Examples of basic amino acids include, but are not limited to arginine and lysine, including both the L and D forms of each.

As used herein, the term "amino sugar" refers to a monosaccharide unit having one or more hydroxyl groups substituted with an amino ($-NH_2$) group. The amino group of an amino sugar can be unsubstituted or substituted with one or more suitable substituents. Examples of amino sugars include, but are not limited to glucosamine and N-methyl-glucamine.

As used herein, the term "quaternary ammonium hydroxide" refers to a positively charged ion having the general structure $[NR_4^+][OH^-]$, wherein R represents an alkyl group. A quaternary ammonium hydroxide is a salt, wherein the cation is a quaternary ammonium ($NR_4$) ion and the anion is a hydroxide ion ($OH^-$). As used herein, the terms "quaternary ammonium ion," "quaternary ammonium cation," and "quaternary ammonium" refer to a positively charged ion having the general structure $[NR_4^+]$, wherein R represents an alkyl group. The four alkyl groups of the quaternary ammonium ion can be the same or different. The alkyl groups can be unsubstituted or substituted with one or more suitable substituents. Examples of quaternary ammonium hydroxides include, but are not limited to, choline hydroxide, tetraethylammonium hydroxide, tetramethylammonium hydroxide, and diethyldimethylammonium hydroxide. Examples of quaternary ammoniums include choline, tetraethylammonium, tetramethylammonium, and diethylammonium.

When a particular group is "substituted," such as an amine, alkyl, aliphatic amine (i.e., alkylamine, alkenylamine, alkynylamine, alicyclic amine), a heterocyclic amine, an arylamine, a heteroarylamine, a polyamine, or amino sugar, that group can have one or more substituents, preferably from one to five substituents, more preferably from one to three substituents, most preferably from one to two substituents. When a group is substituted with more than one substituent, the substituents can be the same or different. Representative examples of suitable substituents for which a particular group can be substituted with include, but are not limited to, hydroxyl (—OH), alkyl, amino (—NH$_2$), and carboxyl (—COOH).

The phrase "pharmaceutically acceptable salt" as used herein means those salts of a compound of interest that are safe and effective for pharmaceutical use in mammals and that possess the desired biological activity. Pharmaceutically acceptable salts include base addition salts, which are salts of basic groups present in the specified compounds, and acid addition salts, which are salts of acid groups present in the specific compounds. The acidic or basic groups can be organic or inorganic. For a review on pharmaceutically acceptable salts see BERGE ET AL., 66 *J. PHARM. SCI.* 1-19 (1977), incorporated herein by reference.

The pharmaceutically acceptable salts of the present invention are preferably base addition salts of nitroxoline. Base addition salts include salts formed with inorganic bases and organic bases. The term "inorganic base," as used herein, has its ordinary meaning as understood by one of ordinary skill in the art and broadly refers to an inorganic compound that can act as a proton acceptor. The term "organic base," as used herein, also has its ordinary meaning as understood by one of ordinary skill in the art and broadly refers to an organic compound that can act as a proton acceptor.

Unless otherwise noted, the term "nitroxoline" refers to a compound having the following chemical structure:

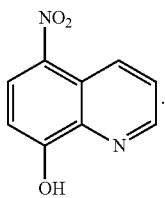 [SMILES: O=[N+]([O-])c1ccc(O)c2ncccc12]

A "base addition salt of nitroxoline" refers to a compound having the following chemical structure:

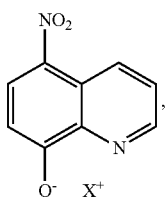

wherein X$^+$ represents a cation, such as a metal cation, an amine cation, ammonium cation (NH$_4^+$), or quaternary ammonium cation.

As used herein, the term "pharmaceutical composition" is intended to encompass a product or composition comprising an active pharmaceutical ingredient in a therapeutically effective amount and a pharmaceutically acceptable carrier.

As used herein, the term "therapeutically effective amount," when referring to an amount of an active pharmaceutical ingredient, means the amount of the active pharmaceutical ingredient that elicits the biological or medicinal response in a tissue system, animal or human that is being sought by a researcher, veterinarian, medical doctor or other clinician, which includes alleviation of the symptoms of the disease, disorder, or condition being treated. In certain embodiments, a "therapeutically effective amount" refers to an amount that that has a prophylactic effect, i.e., prevents or delays the onset of a disease, disorder, or condition. Methods are known in the art for determining the therapeutically effective amount of an active pharmaceutical ingredient according to embodiments of the present invention. Furthermore, and as is also understood by those of ordinary skill in the art, specific dose levels for any particular subject can vary depending upon a variety of factors including the age, body weight, general health, sex, diet, time of administration, route of administration, rate of excretion, any additional therapeutic agents administered in combination therewith and the severity of the disease, disorder, or condition to be treated.

In one general aspect, the present invention relates to a base addition salt of nitroxoline. A base addition salt of nitroxoline is prepared by combining nitroxoline and a base. According to embodiments of the present invention, the base can be an inorganic base or an organic base.

Examples of inorganic bases that can be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

In a preferred embodiment of the present invention, the inorganic base is selected from metal hydroxides and ammonium hydroxide. Preferred metal hydroxides include sodium hydroxide and potassium hydroxide.

Examples of organic bases that can be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines Preferred aliphatic amine bases include alkylamines According to embodiments of the present invention, the base can be a quaternary ammonium hydroxide, wherein one or more of the alkyl groups of the quaternary ammonium ion are optionally substituted with one or more suitable substituents. Preferably, at least one alkyl groups is substituted with one or more hydroxyl groups. Nonlimiting examples of quaternary ammonium hydroxides that can be used in accordance with the present invention include choline hydroxide, trimethylethylammonium hydroxide, tetramethylammonium hydroxide, and is preferably choline hydroxide.

According to embodiments of the present invention, an alkylamine base can be substituted or unsubstituted. Nonlimiting examples of unsubstituted alkylamine bases that can be used in accordance with the present invention include methylamine, ethylamine, diethylamine, and triethylamine A substituted alkylamine base is preferably substituted with one or more hydroxyl groups, and preferably one to three hydroxyl groups. Nonlimiting examples of substituted alkylamine bases that can be used in accordance with the present invention include 2-(diethylamino)ethanol, N,N-dimethylethanolamine (deanol), tromethamine, ethanolamine, and diolamine.

In a preferred embodiment of the present invention, the alkylamine base is selected from diethylamine, diethylamine, 2-diethylaminoethanol, N,N-diemethylethanolamine, tromethamine, ethanolamine, and diolamine According to embodiments of the present invention, an amine base that can be used to form base addition salts of nitroxoline can be a heterocyclic amine Examples of heterocyclic amine bases suitable for use in the present invention include, but are not limited to, piperazine, pyrrolidone, and morpholine. One or more nitrogen atoms of a heterocyclic amine can be substituted with one or more substituents. Preferred substituents include alkyl, such methyl and ethyl, and substituted alkyls, such as methyl or ethyl substituted with a hydroxyl group. Examples of substituted heterocyclic amine bases suitable for use in the present invention include, but are not limited to, 1-(2-hydroxylethyl)pyrrolidine and 4-(2-hydroxyethyl)morpholine.

In a preferred embodiment of the present invention, the heterocyclic amine base is selected from piperazine, 1-(2-hydroxylethylpyrrolidine, and 4-(2-hydroxyethyl)morpholine.

According to embodiments of the present invention, an amine base can also be a basic amino acid. Nonlimiting examples of basic amino acids include arginine and lysine. In a preferred embodiment, the basic amino acid is lysine.

According to other embodiments of the present invention, an amine base can be an amino sugar, preferably N-methylglucamine, or a polyamine, preferably ethylenediamine In other embodiments of the present invention, an amine base that can be used to form base addition salts of nitroxoline can be an arylamine, such as aniline; a heteroarylamine, such as pyridine; an alicyclic amine, such as cyclohexyl; an alkenylamine, such as methyldiallylamine; or an alkynylamine, such as 2-propyne-1-amine Any arylamine, heteroarylamine, alicyclic amine, alkenylamine, or alkynylamine can be used in view of the present disclosure.

According to embodiments of the present invention, a base addition salt of nitroxoline can be an alkali metal salt, an ammonium salt, a quaternary ammonium salt, or an amine salt.

As used herein, "an alkali metal salt" refers to a salt of a compound, wherein the cation of the salt form of the compound is an alkali metal. Preferred nitroxoline alkali metal salts according to the invention include nitroxoline sodium salt and nitroxoline potassium salt.

As used herein, "an ammonium salt" refers to a salt of a compound, wherein the cation of the salt form of the compound is ammonium ($NH_4^+$). When referring to nitroxoline salts, an ammonium salt is nitroxoline ammonium salt.

As used herein, "a quaternary ammonium salt" refers to a salt of a compound, wherein the cation of the salt form of the compound is a quaternary ammonium. Preferred nitroxoline quaternary ammonium salts according to the invention include nitroxoline choline salt.

As used herein, "an amine salt" refers to a salt of a compound, wherein the cation of the salt form of the compound is an amine According to embodiments of the present invention, a nitroxoline amine salt can be a nitroxoline alkylamine salt, a nitroxoline heterocyclic amine salt, a nitroxoline arylamine salt, a nitroxoline heteroarylamine salt, a nitroxoline amino acid salt, a nitroxoline polyamine salt, or a nitroxoline amino sugar salt. Other examples of amine salts of nitroxoline according to the invention include a nitroxoline alkenylamine salt, a nitroxoline alkynylamine salt, and a nitroxoline alicyclic amine salt.

In a particularly preferred embodiment of the present invention, a nitroxoline amine salt is nitroxoline diethylamine salt, nitroxoline ethylenediamine salt, nitroxoline piperazine salt, nitroxoline L-arginine salt, nitroxoline 1-(2-hydroxyethyl)pyrrolidine salt, nitroxoline 2-diethylaminoethanol salt, nitroxoline 4-(2-hydroxyethyl) morpholine salt, nitroxoline N,N-dimethyletanolamine salt, nitroxoline lysine salt, nitroxoline tromethamine salt, nitroxoline N-methylglucamine salt, nitroxoline ethanolamine salt, or nitroxoline diolamine salt.

According to another preferred embodiment of the present invention, a base addition salt of nitroxoline has a chemical structure selected from:

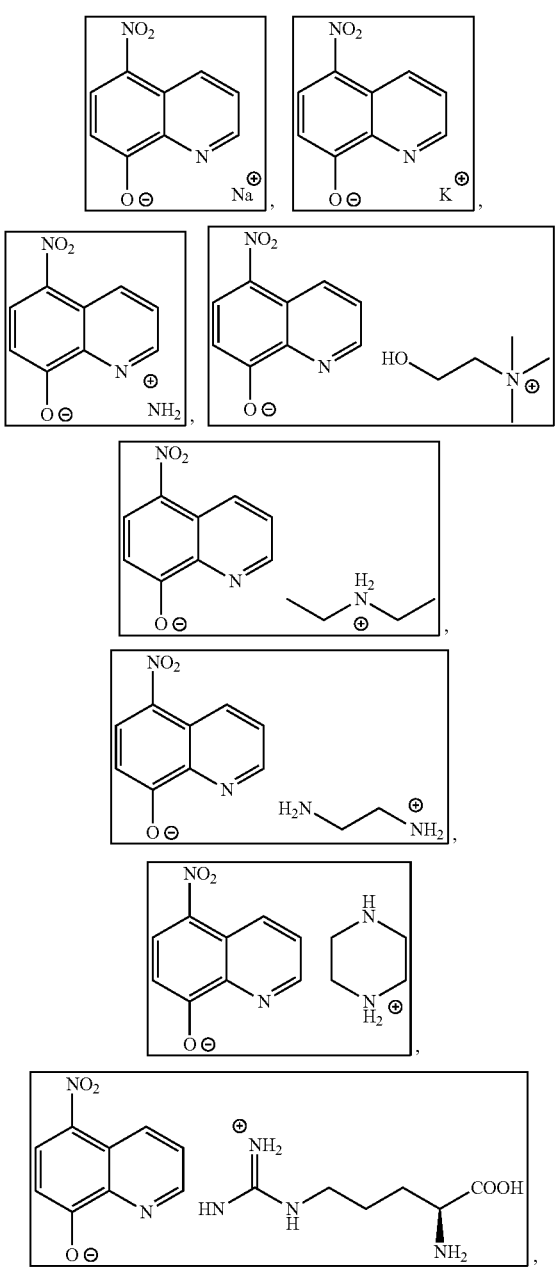

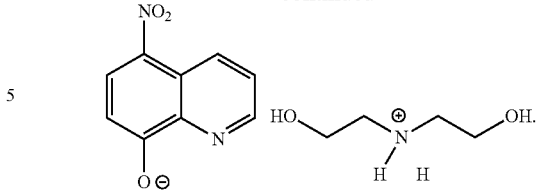

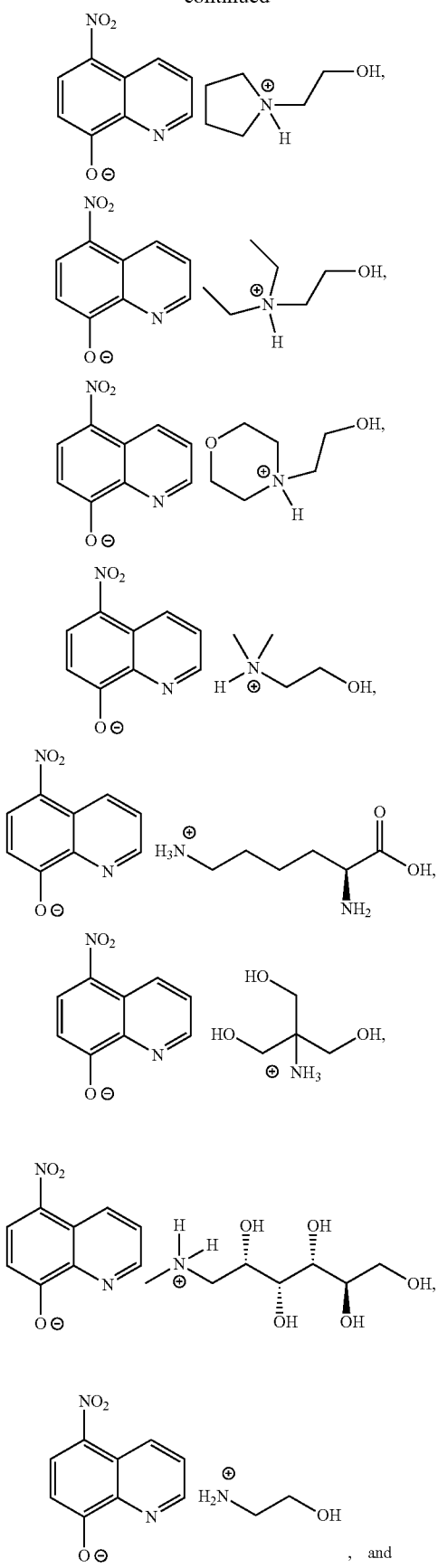

In another general aspect, the present invention provides a base addition salt of nitroxoline, wherein the salt is obtained by mixing nitroxoline and a base. Any base in view of the present disclosure can be used, including organic bases and inorganic bases. Preferably, the base is an amine base, a metal hydroxide, ammonium hydroxide, or a quaternary ammonium hydroxide.

According to embodiments of the present invention, a base addition salt of nitroxoline has improved solubility and improved stability under physiological conditions, e.g., at a pH ranging from about 4.5 to 8, as compared to nitroxoline. The terms "solubility" and "soluble" are used interchangeably, and refer to the solubility of a compound of the invention under physiological conditions in an aqueous medium having a pH between 4.5 and 8. As used herein, "aqueous medium" refers to water, and mixtures of water and other components, provided that the mixture comprises at least 50% by weight, preferably at least 70% by weight, and most preferably at least 90% by weight of water. In one embodiment, the term "stability," when used with reference to a base addition salt of nitroxoline, refers to a decreased propensity to sublime. Base addition salts of nitroxoline according to the invention also have increased drug excretion in the urine of a subject.

Any method known in the art in view of the present disclosure can be used to determine the solubility of base addition salts of nitroxoline according to the invention. For example, the solubility can be determined by the equilibrium solubility method, which entails adding a known mass of a compound to a known volume of an aqueous medium at a defined pH. The resulting solution is agitated (e.g., by stirring) until an equilibrium state is obtained. The solubility can then be determined qualitatively, or quantitatively using known analytical methods (e.g., spectrophotometry). Other methods for determining solubility of a chemical compound are described in Physiochemical Properties of Prostaglandin F2α(Tromethamine Salt): Solubility Behavior, Surface Properties, and Ionization Constants: Journal of Pharmaceutical Sciences, 1973, 62: pages 1680-5; 'General treatment of pH solubility profiles of weak acids and bases. II. Evaluation of thermodynamic parameters from the temperature dependence of solubility profiles applied to a zwitterionic compound: International Journal of Pharmaceutics, 1985, 25: pages 135-145; and U.S. Pat. No. 7,723,119, which are incorporated herein by reference.

According to embodiments of the present invention, a base addition salt of nitroxoline having improved solubility has a solubility of at least 0.1 mg/mL, more preferably, 0.1-1.0 mg/mL, more preferably 1-10 mg/mL, more preferably 30-100 mg/mL, more preferably >100 mg/mL, and even more preferably >1000 mg/mL in an aqueous medium having a pH value between 4.5 and 8, such as a pH of 4.5, 5.0, 5.5, 6.0, 6.5, 7.0, 7.5, or 8.0. According to a preferred embodiment, a base addition salt of nitroxoline having improved solubility has a solubility of at least 0.1 mg/mL, more preferably, 0.1-1.0 mg/mL, more preferably 1-10 mg/mL, more preferably 30-100 mg/mL, more preferably >100 mg/mL, and even more preferably >1000 mg/mL in water.

In another general aspect, the present invention provides methods of preparing a base addition salt of nitroxoline. According to embodiments of the present invention, a method of preparing a base addition salt of nitroxoline comprises mixing nitroxoline and a base in a solvent to obtain the base addition salt, and recovering the base addition salt of nitroxoline from the solvent.

Any base known to one of ordinary skill in the art in view of the present disclosure can be used in method of preparing a base addition salt of nitroxoline according to the invention. Preferred bases include alkali metal hydroxides, ammonium hydroxide, quaternary ammonium hydroxides, and amine bases. Particularly preferred bases include sodium hydroxide, potassium hydroxide, ammonium hydroxide, choline hydroxide, diethylamine, ethylenediamine, piperazine, L-arginine, 1-(2-hydroxyethyl)-pyrrolidine, 2-(diethylamino) ethanol, 2-(hydroxyethyl)-morpholine, N,N-dimethylethanolamine, lysine, tromethamine, N-methylglucamine, ethanolamine, and diolamine.

According to embodiments of the present invention, nitroxoline and a base are mixed in a solvent. The solvent is preferably an organic solvent or a mixture of organic solvents. Examples of organic solvents suitable for use in a method of the present invention include, but are not limited to, alcohols, such as methanol, ethanol and isopropanol; ketones, such as acetone and methylisobutylketone; halogenated solvents, such as dichloromethane; nitriles, such as isobutyronitrile and acetonitrile; aromatic solvents, such as toluene and pyridine; tetrahydrofuran, and mixtures thereof. According to a preferred embodiment of the present invention, a solvent comprises one or more solvents selected from the group consisting of tetrahydrofuran, acetonitrile, methanol, and ethanol.

According to embodiments of the present invention about 1.0 to 2.0 molar equivalents of base relative to nitroxoline are used in a method of preparing a base addition salt of nitroxoline. For example, 1.0, 1.1, 1.2, 1.3, 1.4, 1.5, 1.6, 1.7, 18, 1.9, or 2.0 molar equivalents of base relative to nitroxoline can be used.

The nitroxoline and base can be mixed in a solvent using any method known in the art in view of the present disclosure. The nitroxoline and base can be added to the solvent or mixture of solvents in any order. For example, the nitroxoline can be added to the solvent first followed by addition of the base, the base can be added to the solvent first followed by addition of nitroxoline, or the base and nitroxoline can be added simulataneously to the solvent. The mixture of nitroxoline, base, and solvent can be continuously stirred over the course of the reaction by e.g., using a stir bar, or the mixture can be heated to reflux.

The nitroxoline and base are reacted until the reaction is complete, such as a few hours or overnight. The progress of the reaction can be monitored by any method known in the art in view of the present disclosure, such as thin layer chromatography (TLC). Reactions are typically carried out at room temperature or ambient temperature, i.e., a temperature of 18-25° C., under a nitrogen atmosphere. However, the temperature can be varied depending upon e.g., the particular base used, and the amount of nitroxoline and base, and it is well within the purview of one of ordinary skill in the art to determine the appropriate reaction time and monitor when the reaction has reached completion.

According to embodiments of the present invention, a base addition salt of nitroxoline can be recovered from the solvent by any method known in the art in view of the present disclosure. For example, the base addition salt can be recovered by removing the solvent(s) in vacuo, by filtration, or by crystallization. According to a preferred embodiment, the base addition salt of nitroxoline is recovered by crystallization from the solvent at an appropriate temperature.

Base addition salts can be analyzed by any analytical method known in the art in view of the present disclosure including, but not limited to determination of melting point, $^1$H-NMR, mass spectrometry (MS) and liquid chromatography mass spectrometry (LCMS), and differential scanning calorimetry (DSC).

The present invention also provides a nitroxoline choline salt having a novel crystal form. According to embodiments of the present invention, the crystal has peaks at the diffraction angles (2θ) with an exactness of ±0.2θ: 9.96, 12.12, 17.72, and 20.08 in its powder X-ray diffraction pattern. See FIGS. 4 and 8. Other characteristic peaks of a nitroxoline choline salt of the invention at the diffraction angles (2θ) with an exactness of ±0.2θ include: 7.64, 13.06, 16.6, 18.5, 22.24, 23.06, 23.62, 25.52, and 27.06

In yet another general aspect, the present invention relates to a pharmaceutical composition comprising a therapeutically effective amount of a base addition salt of nitroxoline according to the invention and one or more pharmaceutically acceptable carriers, and methods of making the pharmaceutical composition. A pharmaceutical composition can comprise any base addition salt of nitroxoline according to the invention and described herein.

A pharmaceutical composition according to the invention can be formulated for any form of administration including injectable (intravenous), mucosa, oral (solid and liquid preparations), inhalation, ocular, rectal, topical, or parenteral (infusion, injection, implantation, subcutaneous, intravenous, intraarterial, intramuscular) administration. Examples of solid preparations for oral administration include, but are not limited to, powders, capsules, caplets, gelcaps, and tablets; examples of liquid preparations for oral or mucosal administration include, but are not limited to, suspensions, emulsions, elixirs, and solutions; and examples of topical formulations include, but are not limited to, emulsions, gels, ointments, creams, patches, pastes, foams, lotions, drops, or serums. Examples of preparations for parenteral administration include, but are not limited to injectable solutions, dry products that can be dissolved or suspended in a pharmaceutically acceptable carrier for injection, injectable suspensions, and injectable emulsions. Examples of other suitable compositions include eye drops and other opthalmalic preparations; aerosols, such as nasal sprays or inhalers; liquid dosage forms suitable for parenteral administration; suppositories; and lozenges.

In a preferred embodiment, a pharmaceutical composition is formulated for administration by injection.

Pharmaceutical compositions according to the invention further comprise a pharmaceutically acceptable carrier, such as those widely-employed in the art of drug manufacturing. Pharmaceutically acceptable carriers are non-toxic, and can include one or more of binding agents, such as hydroxypropylmethylcellulose; solubilizing agents, such as povidone and cetylpyridinium chloride; acidifying agents, such as alginic acid; pore forming agents, such as sucrose; lubricants, such as stearyl fumarate; glidants, such as colloidal silicon dioxide; binders, suspending agents, emulsifying agents, diluents, fillers, granulating agents adhesives, disintegrants, antiadherants, glidants, wetting agents, gelling agents, buffers, chelating agents, preservatives, colorants, flavorants, and sweeteners and the like. Pharmaceutically acceptable carriers can take a wide variety of forms dependent on the form of preparation desired for administration, and the amount and type will vary according to the need. One of ordinary skill in the art would readily be able to determine the appropriate carriers to be added to a pharmaceutical composition of the invention in view of the present disclosure.

In certain embodiments, a pharmaceutical composition according to the invention is a sustained-release composition. As used herein, "sustained-release" means that an active pharmaceutical ingredient is released from a pharmaceutical composition at a controlled rate so that therapeutically beneficial blood levels of the active ingredient are maintained over an extended period of time, such as, for example, 1 to 24 hours; 8 to 24 hours; or 12 to 24 hours.

According to embodiments of the present invention, a method of preparing a pharmaceutical composition according to the invention comprises combining a therapeutically effective amount of a base addition salt of nitroxoline and one or more pharmaceutically acceptable carriers. Any method known in the art in view of the present disclosure can be used to combine the base addition salt of nitroxoline with the one or more pharmaceutically acceptable carriers. For example, a pharmaceutical composition according to the invention can be prepared by mixing a therapeutically effective amount of base addition salt of nitroxoline with one or more pharmaceutically acceptable carriers according to conventional pharmaceutical compounding techniques, including but not limited to, conventional mixing, dissolving, granulating, emulsifying, encapsulating, entrapping or lyophilizing processes.

The improved solubility of a base addition salt of nitroxoline according to the invention provides for improved formulations of nitroxoline and improved pharmaceutical compositions of niroxoline. In particular, the improved solubility of base addition salts allows for these nitroxoline salts to be formulated as liquid compositions. Thus, in a preferred embodiment, a pharmaceutical composition according to the invention is a liquid composition. In a particularly preferred embodiment, a pharmaceutical compositions is a liquid composition formulated for injectable administration. Injectable formulations of nitroxoline salts enable nitroxoline to take effect in patients more quickly.

Another general aspect of the invention relates to the use of a pharmaceutical composition according to an embodiment of the present invention for the prevention and/or treatment of a disease, disorder, or condition in a subject in need thereof. According to embodiments of the present invention, a pharmaceutical composition comprising a base addition salt of nitroxoline can be used in a method of treating or preventing any disease, disorder, or condition in a subject for which nitroxoline is known to effective.

As used herein, "subject" means any animal, preferably a mammal, most preferably a human, to whom will be or has been administered a pharmaceutical composition or base addition salt of nitroxoline according to embodiments of the invention. The term "mammal" as used herein, encompasses any mammal Examples of mammals include, but are not limited to, cows, horses, sheep, pigs, cats, dogs, mice, rats, rabbits, guinea pigs, monkeys, humans etc., more preferably a human.

In one embodiment, "treatment" or "treating" refers to an amelioration, propylaxis or reversal of a disease or disorder, or at least one discernible symptom thereof. In another embodiment, "treatment" or "treating" refers to an amelioration, prophylaxis, or reversal of at least one measurable physical parameter related to the disease or disorder being treated, not necessarily discernible in or by the mammal In yet another embodiment, "treatment" or "treating" refers to inhibiting or slowing the progression of a disease or disorder, either physically, e.g., stabilization of a discernible system, physiologically, e.g., stabilization of a physical parameter or both. In yet another embodiment, "treatment" or "treating" refers to delaying the onset of a disease or disorder.

In certain embodiments, compositions of the present invention can be administered as a preventative measure. As used herein "prevention" or "preventing" refers to a reduction of the risk of acquiring a given disease, disorder, or condition.

According to embodiments of the present invention, a method of treating or preventing a disease, disorder, or condition in a subject in need thereof comprises administering to the subject a pharmaceutical composition according to the invention. Any of the pharmaceutical compositions described herein comprising a base addition salt of nitroxoline can be used in a method according to the present invention, and any suitable method of administering the pharmaceutical composition to the subject can be used in view of the present disclosure.

One skilled in the art will recognize that the therapeutically effective amount of a compound to be used in the present invention can vary with factors, such as the particular subject, e.g., age, diet, health, etc., severity and complications and types of symptoms, or the disease, disorder, or condition to be treated or prevented, the formulation used, etc. One of ordinary skill in the art would readily be able to determine a therapeutically effective amount of a compound to administer to a subject in order to elicit the desired biological or medicinal response in the subject in view of the present disclosure.

Any disease, disorder, or condition that nitroxoline is known to be effective against can be treated or prevented by a method of the present invention. Examples of such diseases, disorders or conditions include, but are not limited to, urinary tract infection and diseases associated with angiogenesis, e.g., tumor or cancer. In certain embodiments, a method of the present invention can be used to inhibit angiogenesis or the growth and invasion of cancer.

As used herein, "a urinary tract infection" refers to an infection of any part of the urinary system, including the kidney, ureters, urethra, and bladder. Typically, a urinary tract infection involves the lower part of the urinary system, i.e., the bladder and urethra. Urinary tract infection encompasses cystitis (i.e., bladder infection), pyelonephritis (i.e., infection of one or more kidneys), and urethritis (i.e., urethra infection). A urinary tract infection can be caused by bacterial species from the genera *Escherichia, Staphylococcus, Klebsiella, Proteus, Pseudomonas,* and *Enterobacter*; viruses; or fungus. Urinary tract infections are commonly caused by *Escherichia coli.*

Cancer is an unregulated proliferation of cells due to loss of normal controls, resulting in abnormal growth, lack of differentiation, local tissue invasion, and often, metastasis. Tumor is an abnormal growth of cells or tissues which may be benign or malignant. Tumors or cancers that can be treated with a pharmaceutical composition of the present invention include, but are not limited to, actinic keratosis, adrenal cancer, basal cell carcinoma, bladder cancer, brain tumor, breast cancer, cervical cancer, colon cancer, esophagus cancer, head and neck cancer, Hodgkin disease, Kaposi's sarcoma, larynx cancer, leukemia, lung carcinoma, liver cancer, melanoma, multiple myeloma, mesothelioma, ovarian cancer, pancreatic cancer, prostate cancer, renal cancer, rectal cancer, stomach cancer, squamous cell carcinoma, thyroid cancer, testicular cancer, thyroid cancer, and uterine cancer, etc.

Base addition salts of nitroxoline according to the invention exhibit an unexpected increase in urinary excretion as compared to nitroxoline. Thus, in a preferred embodiment of the present invention, the disease, disorder or condition to be treated or prevented is a urinary tract infection.

The present invention provides a method of providing a urinary protective effect. According to embodiments of the present invention, the method comprises administering to a subject in need thereof a pharmaceutical composition comprising a base addition salt of nitroxoline according to the invention. In a preferred embodiment, a method of providing a urinary protective effect provides a protective effect against a urinary tract infection.

The following examples according to embodiments of the present invention are to further illustrate the nature of the invention. It should be understood that the following examples do not limit the invention and that the scope of the invention is to be determined by the appended claims.

EXAMPLES

Unless stated otherwise, temperatures are given in degrees Celsius (° C.); operations were carried out at room temperature or ambient temperature, abbreviated "rt," or "RT," (typically a range of from about 18-25° C.; evaporation of solvent was carried out using a rotary evaporator under reduced pressure (typically, 4.5-30 mm Hg) with a bath temperature of up to 60° C.; the course of reactions was typically monitored by thin layer chromatography (TLC); melting points are uncorrected; and products exhibited satisfactory 1H-NMR and/or microanalytical data. The following conventional abbreviations are also used throughout the examples: L (liters), mL (milliliters), mmol (millimoles), M (molarity, mol/L), g (grams), mg (milligrams), min (minutes), h (hours), eq. (equivalents), dd (doublets of doublets), d (doublets), s (singlet), t (triplets), m (multiples)).

Unless otherwise specified, all solvents and reagents were purchased from suppliers and used without further purification. Reactions were conducted under a blanket of nitrogen unless otherwise stated. Compounds were visualized under UV lamp (254 nM). 1H NMR spectra were recorded on a 300 MHz NMR at 300 MHz.

Examples 1-22 describe methods of preparing of different salts of nitroxoline by treating nitroxoline with base or acid reagents in various solvent systems. By way of example and not limitation, Table 1 shows examples of bases and solvents that can be used to make nitroxoline salts, including novel base addition salts of nitroxoline according to embodiments of the present invention.

TABLE 1

Methods for preparing nitroxoline salts according to the present invention.

| APL Codes | Acid or Base Added to Nitroxoline | Solvents | Structure of Nitroxoline Salt |
|---|---|---|---|
| 1202[1] | n/a | n/a | |
| 1071 | HCl | MeOH or water | |
| 1074 | HBr | THF or water | |
| 1075 | $HNO_3$ | THF | |

TABLE 1-continued
Methods for preparing nitroxoline salts according to the present invention.
| APL Codes | Acid or Base Added to Nitroxoline | Solvents | Structure of Nitroxoline Salt |
|---|---|---|---|
| 1076 | PhSO$_3$H | THF | 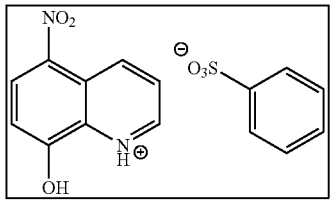 |
| 1072 | NaOH | EtOH | 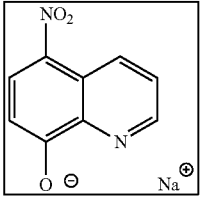 [SMILES: O=[N+]([O-])c1ccc([O-])c2ncccc12 ; [Na+]] |
| 1077 | KOH | THF | 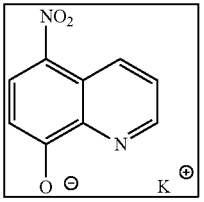 [SMILES: O=[N+]([O-])c1ccc([O-])c2ncccc12 ; [K+]] |
| 1073 | NH$_4$OH | THF | 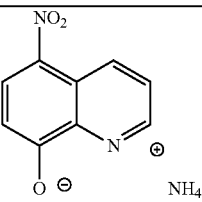 |
| 1078 | Choline hydroxide | Isopropanol | 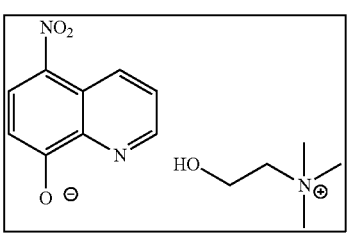 |
| 1079 | Diethylamine | THF | 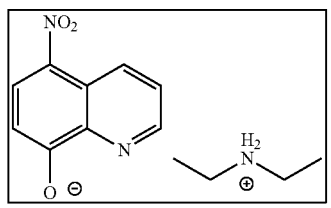 |
| 1080 | Ethylene-diamine | THF | 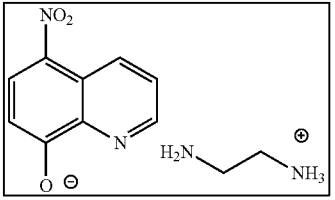 |

TABLE 1-continued

Methods for preparing nitroxoline salts according to the present invention.

| APL Codes | Acid or Base Added to Nitroxoline | Solvents | Structure of Nitroxoline Salt |
|---|---|---|---|
| 1081 | Piperazine | THF | |
| 1082 | L-Arginine | Isopropanol | |
| 1088 | 1-(2-Hydroxyethyl)-pyrrolidine | THF | |
| 1089 | 2-(Diethylamino)ethanol | THF | |
| 1090 | 4-(2-hydroxyethyl)-morpholine | THF | |
| 1091 | N,N-dimethylethanol-amine | THF | |
| 1092 | lysine | Isopropanol | |

TABLE 1-continued

Methods for preparing nitroxoline salts according to the present invention.

| APL Codes | Acid or Base Added to Nitroxoline | Solvents | Structure of Nitroxoline Salt |
|---|---|---|---|
| 1093 | tromethamine | Isopropanol | [nitroxoline anion with tromethamine cation] |
| 1116 | N-methylglucamine | THF | [nitroxoline anion with N-methylglucamine cation] |
| 1117 | Ethanolamine | THF | [nitroxoline anion with ethanolamine cation] |
| 1118 | Diolamine | THF | [nitroxoline anion with diethanolamine cation] |

[1] entry refers to nitroxoline

Example 1

Method for Making Nitroxoline HCl Salt (APL-1071)

To a suspension of nitroxoline (0.2 g, 1.05 mmol) in 4 mL MeOH, 1.3 eq. 36% HCl aqueous solution were slowly added. An orange solid was obtained by filtration (yield: 0.15 g, 63%). Alternatively, nitroxoline (0.5 g, 2.63 mmol) was refluxed in 25 mL 36% HCl aqueous solution. A clear solution was formed, then cooled. A yellow solid (yield: 0.33 g, 55%) was obtained by filtration. mp: 236-240° C.; and $^1$H-NMR (300 MHz, DMSO-d6) δ: 9.20 (d, 1H), 9.03-9.05 (dd, 1H), 8.55-8.58 (d, 1H), 7.91-7.95 (m, 1H), 7.25-7.28 (d, 1H).

Example 2

Method for Making Nitroxoline HBr Salt (APL-1074)

To a solution of nitroxoline (0.2 g, 1.05 mmol) in 4 mL THF, 1.5 eq. 40% HBr aqueous solution were slowly added. A yellow solid was obtained by filtration (yield: 0.17 g, 60%). Alternatively, nitroxoline (0.5 g, 2.63 mmol) was refluxed in 25 mL 40% HBr aqueous solution. A clear solution was formed, then cooled. A yellow solid (yield: 0.43 g, 60%) was obtained by filtration. mp: 274-276° C.; and $^1$H-NMR (300 MHz, DMSO-d6) δ: 9.24-9.28 (dd, 1H), 9.05-9.07 (dd, 1H), 8.56-8.59 (d, 1H), 7.95-7.99 (m, 1H), 7.24-7.27 (d, 1H).

Example 3

Method for Making Nitroxoline HNO$_3$ Salt (APL-1075)

To a solution of nitroxoline (0.2 g, 1.05 mmol) in 4 mL THF, 2.0 eq. 60% HNO$_3$ aqueous solution were slowly added. A dark yellow solid was obtained by filtration (yield: 0.21 g, 79%). mp: >290° C.; and $^1$H-NMR (300 MHz, DMSO-d6) δ: 9.20-9.23 (dd, 1H), 9.03-9.05 (dd, 1H), 8.55-8.58 (d, 1H), 7.91-7.96 (m, 1H), 7.21-7.24 (d, 1H).

Example 4

Method for Making Nitroxoline PhSO$_3$H Salt APL-1076

To a solution of nitroxoline (0.2 g, 1.05 mmol) in 4 mL THF, 1.5 eq. benzenesulfonic acid were slowly added. A light yellow solid was obtained by filtration (yield: 0.24 g, 65%). mp: 238-241° C.; and $^1$H-NMR (300 MHz, DMSO-d6) δ: 9.24-9.27 (dd, 1H), 9.05-9.06 (dd, 1H), 8.56-8.59 (d, 1H), 7.95-7.99 (m, 1H), 7.58-7.63 (m, 2H), 7.32-7.36 (m, 3H), 7.23-7.26 (d, 1H).

Example 5

Method for Making Nitroxoline Sodium Salt (APL-1072)

To a suspension of nitroxoline (0.2 g, 1.05 mmol) in 4 mL EtOH, 1.5 eq. sodium hydroxide were slowly added. An orange solid was obtained by filtration (yield: 0.15 g, 67%). mp: >290° C.; and $^1$H-NMR (300 MHz, DMSO-d6) δ: 9.43-9.46 (dd, 1H), 8.53-8.55 (dd, 1H), 8.39-8.42 (d, 1H), 7.55-7.59 (m, 1H), 6.22-6.26 (d, 1H).

Example 6

Method for Making Nitroxoline Potassium Salt (APL-1077)

To a solution of nitroxoline (0.2 g, 1.05 mmol) in 4 mL THF, 1.5 eq. potassium hydroxide in 1 mL water were slowly added. An orange solid was obtained by filtration (yield: 0.20 g, 83%). mp: >290° C.; and $^1$H-NMR (300 MHz, DMSO-d6) δ: 9.43-9.46 (dd, 1H), 8.51-8.53 (dd, 1H), 8.33-8.36 (d, 1H), 7.48-7.52 (m, 1H), 6.11-6.14 (d, 1H).

Example 7

Method for Making Nitroxoline Ammonium Salt (APL-1073)

To a solution of nitroxoline (0.2 g, 1.05 mmol) in 4 mL THF, 1.4 eq ammonia hydroxide were slowly added. An orange solid was obtained by filtration (yield: 0.17 g, 78%). mp: 188-192° C.; and $^1$H-NMR (300 MHz, DMSO-d6) δ: 9.40-9.43 (dd, 1H), 8.56-8.57 (dd, 1H), 8.37-8.40 (d, 1H), 7.52-7.57 (m, 1H), 6.21-6.25 (d, 1H).

Example 8

Method for Making Nitroxoline Choline Salt (APL-1078)

Figure 2:
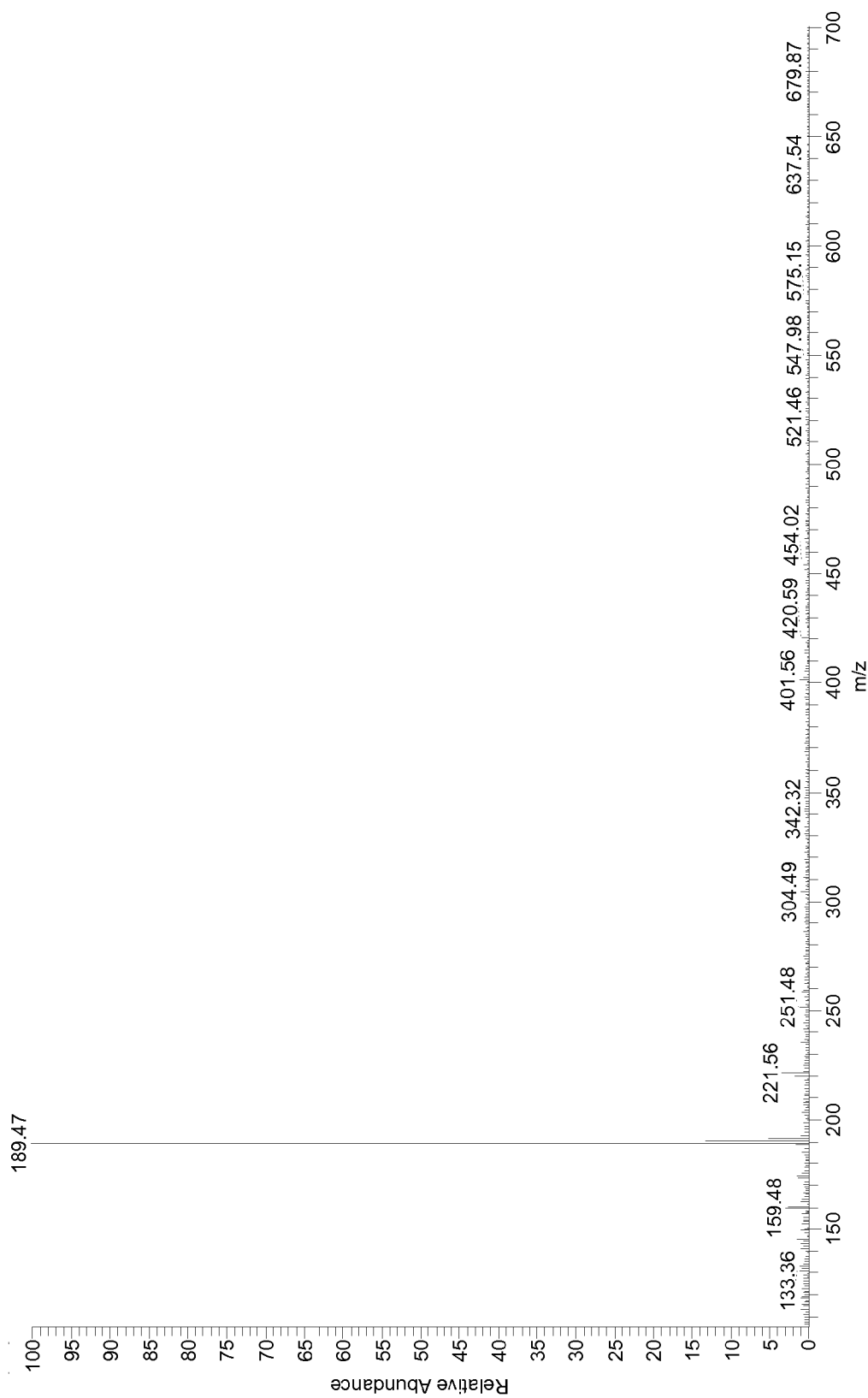
FIG. 2 provides the mass spectrum of nitroxoline choline salt.
Figure 3:
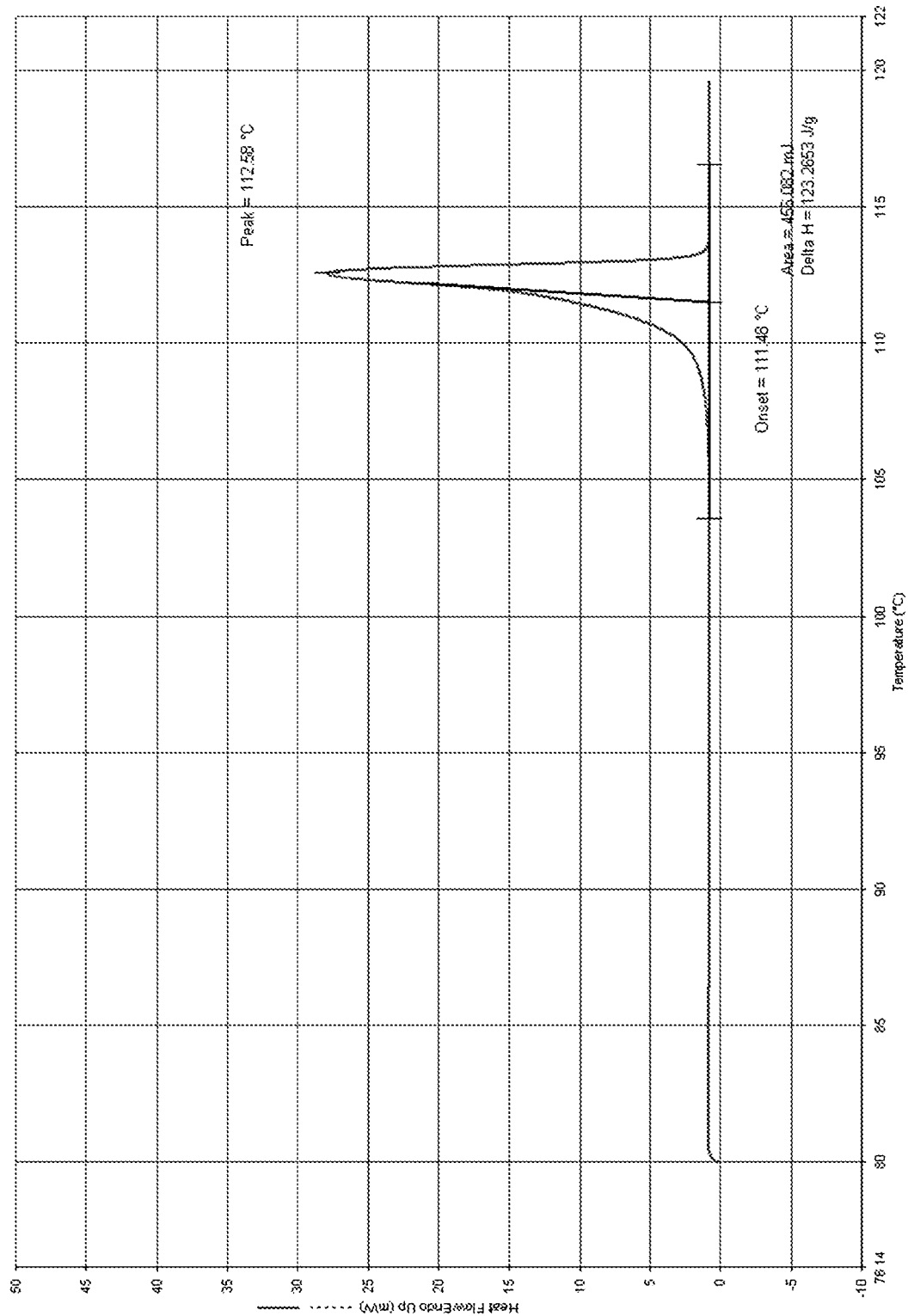
FIG. 3 provides the differential scanning calorimetry (DSC) of nitroxoline choline salt.
Figure 4:
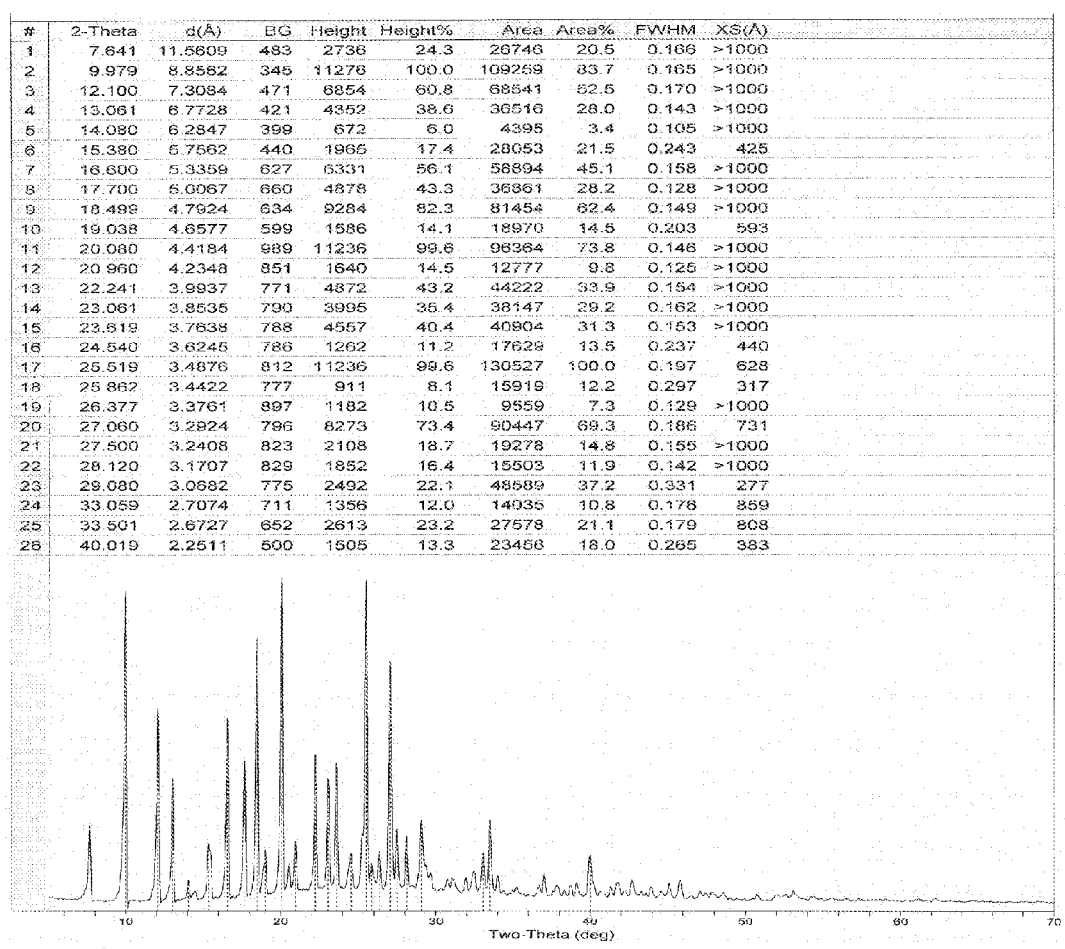
FIG. 4 provides the powder X-ray powder (pXRD) of nitroxoline choline salt.

A suspension of nitroxoline (25 g, 131.6 mmol) and choline (36.5 g, 150 7 mmol, in 50% aqueous solution) in isopropyl alcohol (IPA) (350 mL) was refluxed for 1 h. A clear solution was obtained. After removal of the solvents in vacuo, IPA (110 mL) was added. The suspension was then heated to 60° C. to give a clear solution. After cooling to room temperature, a yellow solid (29 g) was obtained by filtration (yield: 75.6%). mp: 110-113° C.; $^1$H-NMR (300 MHz, DMSO-d6) δ: 9.45-9.42 (dd, J=8.7 Hz, 1.62 Hz, 1H), 8.51-8.50 (dd, J=4.00 Hz, 1.55 Hz, 1H),8.35-8.32 (d, J=9.93 Hz, 1H), 7.50-7.46 (m,1H), 6.12-6.09 (d, J=9.90 Hz, 1H), 5.34-5.31 (t, J=4.55 Hz, 1H), 3.84 (m, 2H), 3.41-3.38 (t, J=5.25 Hz, 2H), 3.10 (s, 9H) (FIG. 1); LC/MS (M-1): 189 (FIG. 2); DSC: 112.50° C. (FIG. 3); and powder X-ray diffraction (pXRD) 2θ and peak intensity values are shown in FIG. 4.

Example 9

Method for Making Nitroxoline Diethylamine Salt (APL-1079)

To a solution of nitroxoline (0.2 g, 1.05 mmol) in 4 mL THF, 1.8 eq. diethylamine were slowly added. A yellow solid was obtained by filtration (yield: 0.20 g, 72%). mp: 160-168° C.; and $^1$H-NMR (300 MHz, DMSO-d6) δ: 9.41-9.44 (dd, 1H), 8.57-8.59 (dd, 1H), 8.37-8.40 (d, 1H), 7.53-7.57 (m, 1H), 6.22-6.25 (d, 1H), 2.92-2.99 (dd, 4H), 1.13-1.18 (t, 6H).

Example 10

Method for Making Nitroxoline Ethylenediamine Salt (APL-1080)

To a solution of nitroxoline (0.2 g, 1.05 mmol) in 4 mL THF, 1.9 eq. ethylendiamine were slowly added. A yellow solid was obtained by filtration (yield: 0.20 g, 77%). mp: 204-206° C.; and $^1$H-NMR (300 MHz, DMSO-d6) δ: 9.40-9.43 (dd, 1H), 8.55-8.57 (dd, 1H), 8.37-8.40 (d, 1H), 7.52-7.56 (m, 1H), 6.22-6.26 (d, 1H), 2.84 (s, 4H).

Example 11

Method for Making Nitroxoline Piperazine Salt (APL-1081)

To a solution of nitroxoline (0.2 g, 1.05 mmol) in 4 mL THF, 1.5 eq. piperazine were slowly added. A yellow solid was obtained by filtration (yield: 0.25 g, 86%). mp: 206-210° C.; and $^1$H-NMR (300 MHz, DMSO-d6) δ: 9.41-9.44 (dd, 1H), 8.58-8.59 (d, 1H), 8.36-8.40 (d, 1H), 7.53-7.57 (m, 1H), 6.23-6.26 (d, 1H), 2.91 (s, 8H).

Example 12

Method for Making Nitroxoline L-Arginine Salt (APL-1082)

A solution of nitroxoline (0.2 g, 1.05 mmol) and 1.0 eq. L-Arginine in 4 mL IPA was refluxed overnight. After cooling to room temperature, a yellow solid was obtained by filtration (yield: 0.33 g, 78%). mp: 198-200° C.; and $^1$H-NMR (300 MHz, MeOD-d4) δ: 9.46-9.49 (dd, 1H), 8.71-8.72 (dd, 1H), 8.58-8.61 (d, 1H), 7.61-7.70 (m, 1H), 6.67-6.70 (d, 1H), 3.52-3.56 (t, 1H), 3.22-3.25 (t, 2H), 1.81-1.89 (m, 2H), 1.67-1.77 (m, 2H).

Example 13

Recrystallization of Nitroxoline Choline Salt in CH$_3$CN

Figure 5:
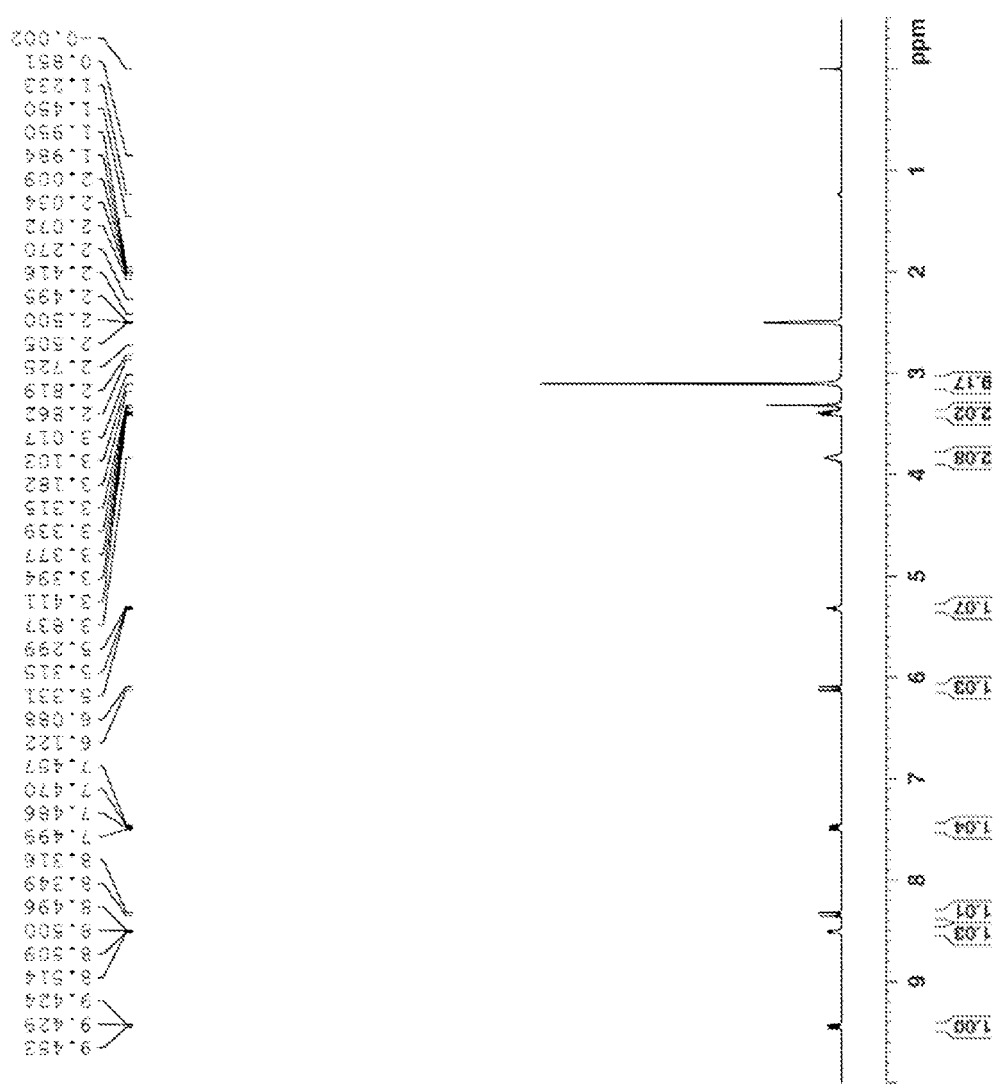
FIG. 5 provides the $^1$H-NMR spectrum of recrystallized nitroxoline choline salt.
Figure 6:
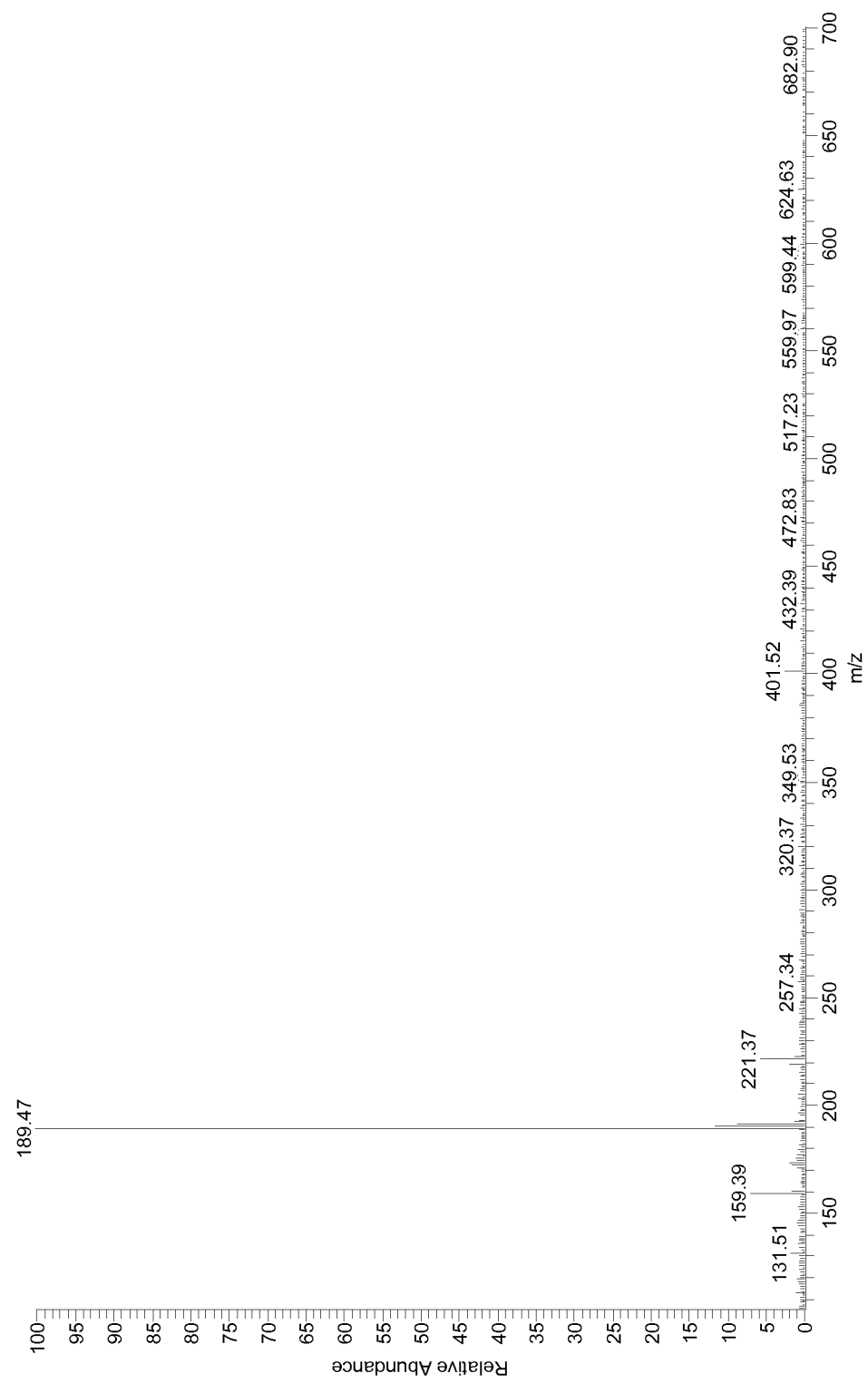
FIG. 6 provides the mass spectrum of recrystallized nitroxoline choline Salt.
Figure 7:
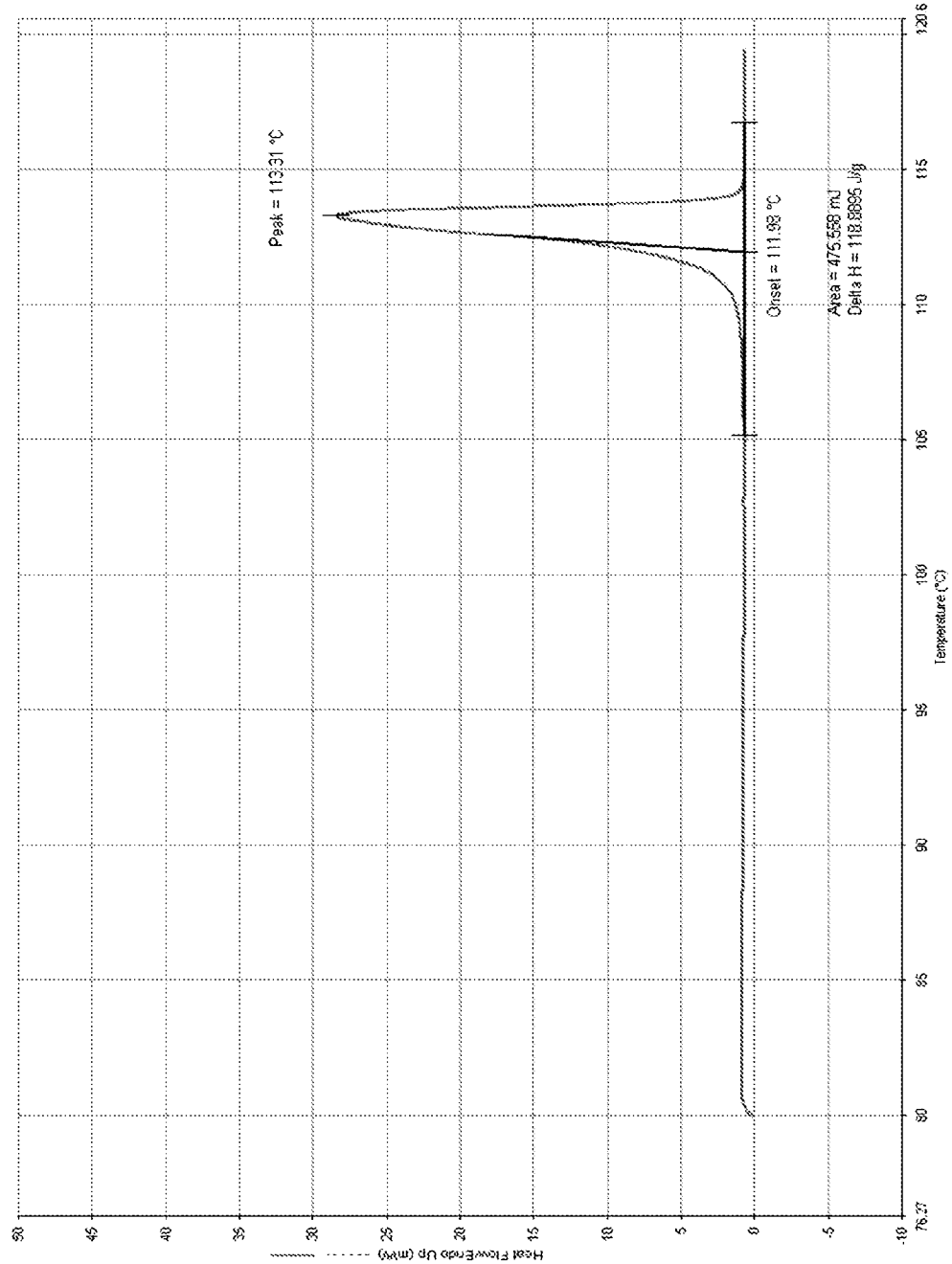
FIG. 7 provides the DSC of recrystallized nitroxoline choline salt.
Figure 8:
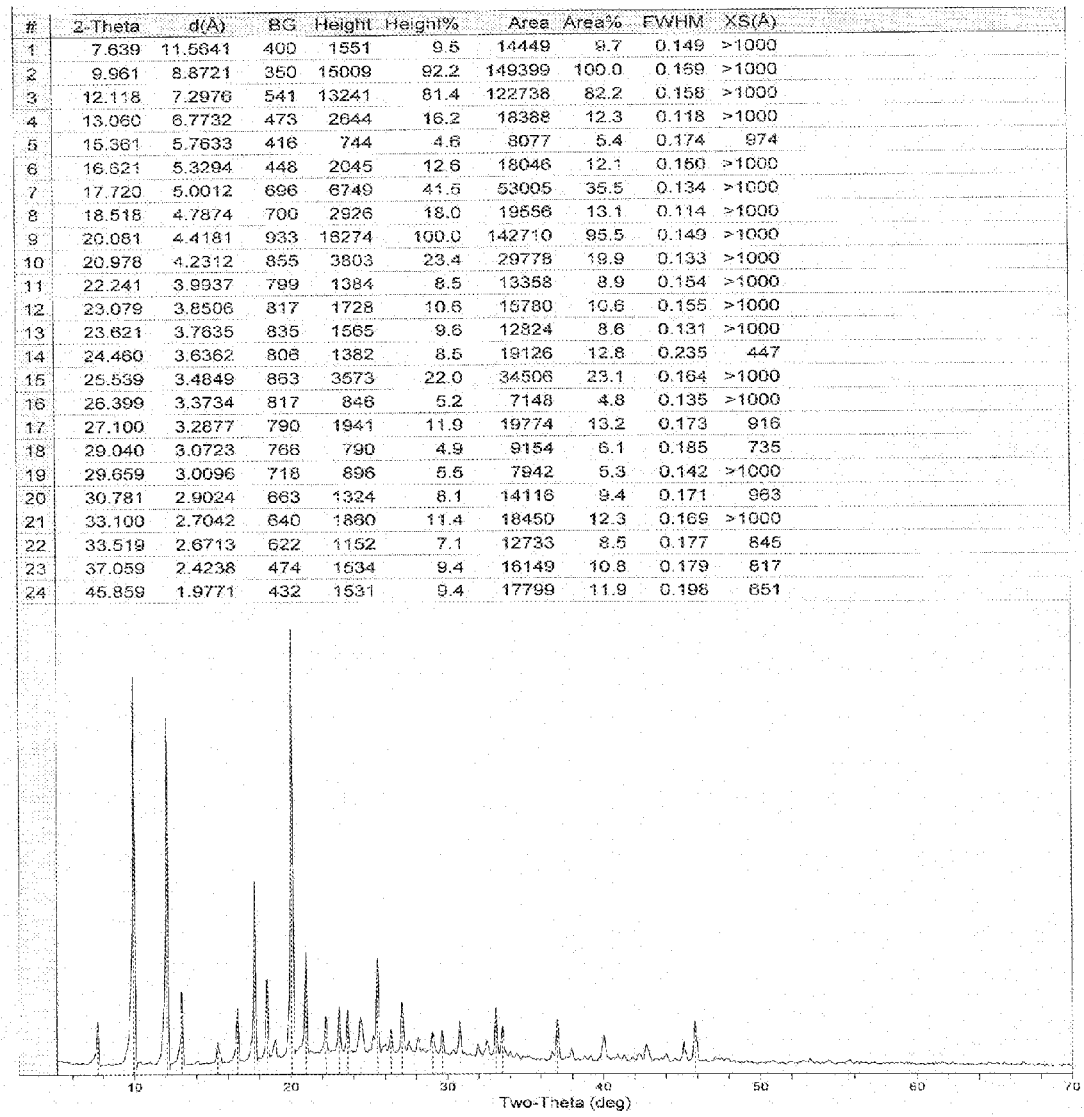
FIG. 8 provides the pXRD of recrystallized nitroxoline choline salt.

A suspension of nitroxoline choline hydroxide salt (3.5 g) in CH$_3$CN (100 mL) was heated to 50-60° C. to form a clear solution. After cooling to room temperature, crystals (2.5 g) were obtained by filtration as a light yellow solid (yield: 71.4%). mp: 110-113° C.; $^1$H-NMR (300 MHz, DMSO-d6) δ: 9.46-9.42 (dd, J=8.70 Hz, 1.53 Hz, 1H), 8.51-8.50 (dd, J=3.99 Hz, 1.41 Hz,1H), 8.35-8.32 (d, J=8.33 Hz, 1H), 7.50-7.46 (m, 1H), 6.12-6.09 (d, J=9.90 Hz,1H), 5.33-5.30 (t, J=4.68 Hz,1H), 3.84 (m, 2H), 3.41-3.38 (t, J=5.22 Hz, 2H), 3.10(s, 9H) (FIG. 5); LC/MS (M-1): 189 (FIG. 6); DSC: 113.31° C. (FIG. 7); and powder X-ray diffraction (pXRD) 2θ and peak intensity values are shown in FIG. 8.

Example 14

Method for Making Nitroxoline 1-(2-Hydroxyethyl)-pyrrolidine Salt (APL-1088)

To a solution of nitroxoline (1.0 g, 5.26 mmol) in THF (20 mL), 1-(2-hydroxyethyl)-pyrrolidine (1.09 g, 9.46 mmol)

was added at room temperature. The mixture was stirred overnight at room temperature, and the resulting suspension was filtrated to yield a yellow solid (0.8 g, 50% yield). mp: 102-104° C.; $^1$H-NMR (300 MHz, DMSO-d6) δ: 9.34 (d, 1H), 8.69 (d,1H), 8.40-8.43 (d, 1H), 7.61-7.65 (m, 1H), 6.47-6.50 (d,1H), 3.59-3.63 (m, 2H), 2.97-3.03 (m, 6H), 1.77-1.84(m, 4H); and LC/MS (M-1): 189.46.

Example 15

Method for Making Nitroxoline 2-(Diethylamino)ethanol Salt (APL-1089)

To a solution of nitroxoline (1.0 g, 5.26 mmol) in THF (20 mL), 2-(diethylamino)ethanol (1.1 g, 9.46 mmol) was added at room temperature. The mixture was stirred overnight at room temperature, and the resulting suspension was filtrated to yield a yellow solid (0.7 g, 43% yield). mp: 76-78° C.; $^1$H-NMR (300 MHz, DMSO-d6) δ: 9.32 (d, 1H), 8.70-8.72 (d,1H), 8.41-8.44 (d, 1H), 7.62-7.66 (m, 1H), 6.50-6.53 (d,1H), 3.59-3.62 (m, 2H), 2.87-2.95 (m, 6H), 1.07-1.18(m, 6H); and LC/MS (M-1): 189.38.

Example 16

Method for Making Nitroxoline 4-(2-hydroxyethyl)-morpholine Salt (APL-1090)

To a solution of nitroxoline (1.0 g, 5.26 mmol) in THF (20 mL), 4-(2-hydroxyethyl)-morpholine (0.99 g, 7.54 mmol) was added at room temperature. The mixture was stirred overnight at room temperature, and after cooling to 0° C., the resulting suspension was filtrated to yield a yellow solid (0.8 g, 47% yield). mp: 124-128° C.; $^1$H-NMR (300 MHz, DMSO-d6) δ: 9.18 (d, 1H), 8.95-8.96 (d,1H), 8.51-8.54 (d, 1H), 7.81-7.86 (m, 1H), 7.04-7.07 (d,1H), 3.50-3.60 (m, 6H), 2.45-2.50 (m, 2H); and LC/MS (M-1): 189.44.

Example 17

Method for Making Nitroxoline (N,N-dimethylethanolamine) salt (APL-1091)

To a solution of nitroxoline (1.0 g, 5.26 mmol) in THF (20 mL), N,N-dimethylethanolamine (0.84 g, 9.46 mmol) was added at room temperature. The mixture was stirred overnight at room temperature, and the resulting suspension was filtrated to yield a yellow solid (0.8 g, 55% yield). mp: 120-124° C.; $^1$H-NMR (300 MHz, DMSO-d6) δ: 9.31 (d, 1H), 8.73 (d,1H), 8.42-8.45 (d, 1H), 7.64-7.68 (m, 1H), 6.55-6.58 (d,1H), 3.58-3.62 (t, 2H), 2.79-2.83 (t, 2H); and LC/MS (M-1): 189.38.

Example 18

Method for Making Nitroxoline Lysine Salt (APL-1092)

To a solution of nitroxoline (1.0 g, 5.26 mmol) in isopropanol (20 mL), lysine (1.15 g, 7.87 mmol) was added at room temperature. The mixture was heated to reflux and stirred overnight. The solution was cooled to room temperature, and the resulting suspension was filtrated to yield a yellow solid (1.2 g, 68% yield). mp: 188-190° C.; $^1$H-NMR (300 MHz, DMSO-d6) δ: 9.42 (d, 1H), 8.56 (d,1H), 8.35-8.38 (d, 1H), 7.51-7.53 (m, 1H), 6.17-6.20 (d,1H), 3.17-3.20 (m, 2H), 2.76-2.80 (t, 2H), 1.40-1.66 (m, 6H); and LC/MS (M-1): 189.41.

Example 19

Method for Making Nitroxoline Tromethamine Salt (APL-1093)

To a solution of nitroxoline (1.0 g, 5.26 mmol) in isopropanol (20 mL), tromethamine (0.95 g, 7.87 mmol) was added at room temperature. The mixture was heated to reflux and stirred for one hour. The solution was cooled to room temperature, and the resulting suspension was filtrated to yield a yellow solid (1.0 g, 61% yield). mp: 154-158° C.; $^1$H-NMR (300 MHz, DMSO-d6) δ: 9.40-9.43 (m, 1H), 8.57-8.58 (m,1H), 8.35-8.38 (m, 1H), 7.52-7.56 (m, 1H), 6.22-6.26 (d,1H), 5.10 (m, 3H), 3.63 (m, 6H); and LC/MS (M-1): 189.40.

Example 20

Method for Making Nitroxoline N-methylglucamine Salt (APL-1116)

To a solution of nitroxoline (3.0 g, 15 8 mmol) in THF (20 mL), N-methylglucamine (5.54 g, 28.4 mmol) was added at room temperature. The mixture was heated to 70° C. and stirred for several hours. The solution was cooled to room temperature, and the resulting suspension was filtrated to yield a yellow solid (4.5 g, 74% yield). mp: 173-176° C.; $^1$H-NMR (300 MHz, DMSO-d6) δ: 9.40 (m, 1H), 8.58 (dd, J=1.5 Hz, J=3.9 Hz, 1H), 8.37 (d, J=9.9 Hz, 1H), 7.54 (dd, J=3.9 Hz, J=9.0 Hz, 1H), 6.24 (d, J=9.6 Hz, 1H), 3.70-3.35 (m, 4H), 3.10-2.85 (m, 2H), 2.54 (s, 3H); and LC/MS (M-1): 189.47.

Example 21

Method for Making Nitroxoline Ethanolamine Salt (APL-1117)

To a solution of nitroxoline (3.0 g, 15.8 mmol) in THF (20 mL), ethanolamine (1.45 g, 23.7 mmol) was added at room temperature. The mixture was heated to 70° C. and stirred for several hours. The solution was cooled to room temperature, and the resulting suspension was filtrated to yield a yellow solid (3.4 g, 76% yield). mp: 178-180° C.; $^1$H-NMR (300 MHz, DMSO-d6) δ: 9.43 (dd, J=2.5 Hz, J=8.9 Hz, 1H), 8.57 (dd, J=2.5 Hz, J=4.2 Hz, 1H), 8.39 (d, J=9.9 Hz, 1H), 7.55 (dd, J=4.2 Hz, J=8.9 Hz, 1H), 6.23 (d, J=9.9 Hz, 1H), 3.60 (t, J=5.6 Hz, 2H), 2.19 (t, J=5.6 Hz, 2H); and LC/MS (M-1): 189.43.

Example 22

Method for Making Nitroxoline Diolamine Salt (APL-1118)

To a solution of nitroxoline (3.0 g, 15.8 mmol) in THF (20 mL), diolamine (2.49 g, 23.7 mmol) was added at room temperature. The mixture was heated to 70° C. and stirred for several hours. The solution was cooled to room temperature, and the resulting suspension was filtrated to yield a yellow solid (3.39 g, 62% yield). mp: 142-144° C.; $^1$H-NMR (300 MHz, DMSO-d6) δ: 9.41 (dd, J=1.5 Hz, J=8.7 Hz, 1H), 8.61 (dd, J=1.5 Hz, J=3.9 Hz, 1H), 8.40 (d, J=9.6 Hz, 1H), 7.58 (dd, J=3.9 Hz, J=8.7 Hz, 1H), 6.31 (d, J=9.6 Hz, 1H), 3.64 (t, J=5.7 Hz, 2H), 3.00 (t, J=5.7 Hz, 2H); and LC/MS (M-1): 189.51.

Example 23

Solubility Tests of Nitroxoline and Nitroxoline Salts

The solubility of nitroxoline and nitroxoline salts was determined as described below. The results are summarized in Table 2.

1) Aqueous buffer solutions with varying pH were prepared as follows:
   i. Water: distilled water;
   ii. pH=1.2 buffer: 7.65 mL 36.5% HCl solution was diluted to 1000 mL with water;
   iii. pH=4.5 buffer: 18 g sodium acetate and 9.8 mL acetic acid were diluted to 1000 mL with water;
   iv. pH=5.0 buffer: sodium hydroxide was added to 0.2 mol/L monosodium phosphate ($NaH_2PO_4$) solution until the pH was adjusted to 5.0;
   v. pH=6.0 buffer: 18 g sodium acetate were added into 20 mL acetic acid solution (1 M), and the mixture was diluted to 500 mL with water;
   vi. pH=6.8 buffer: 250 mL of 0.2 M monopotassium phosphate ($KH_2PO_4$) solution were added to 118 mL of 0.2 M sodium hydroxide solution, and the mixture was diluted to 1000 mL with water;
   vii. pH=7.4 buffer: 1.36 g monopotassium phosphate ($KH_2PO_4$) were added to 79 mL of 0.1 M sodium hydroxide solution, and the mixture was diluted to 200 mL with water; and
   viii. pH=8.0 buffer: 5.59 g potassium biphosphate ($K_2HPO_4$) and 0.41 g monopotassium phosphate ($KH_2PO_4$) were added to 1000 mL water and mixed.

2) Solubility tests were performed generally as follows:
Under a temperature of 25±2° C., 10 mg of each salt sample was weighed and added to a 100 mL volumetric bottle. 0.25 mL buffer was added to the bottle, which was shaken vigorously for 30 seconds every 5 min. Sample dissolution was observed for 30 min. If the sample was completely dissolved, its solubility was marked as ">30 mg/mL".

If the sample was not completely dissolved, 0.7 mL of the same buffer was added, and dissolution was observed by the same shaking procedure. If the sample was completely dissolved, its solubility was marked as "10<<30 mg/mL".

If the sample was not completely dissolved, 8.5 mL of the same buffer was added, and dissolution was observed by the same shaking procedure. If the sample was completely dissolved, its solubility was marked as "1<<10 mg/mL".

If the sample was not completely dissolved, 85 mL of the same buffer was added, and dissolution was observed by the same shaking procedure. If the sample was completely dissolved, its solubility was marked as "0.1<<1 mg/mL".

If the sample was still not completely dissolved, its solubility was marked as "<0.1 mg/mL".

Solubility Tests of APL-1078 (Nitroxoline Choline Salt).

Because 10 mg APL-1078 was completely dissolved in 0.25 mL water and pH=8.0 buffer, its solubility was marked as >30 mg/mL. In a second test, 50 mg APL-1078 was added into a 100 mL volumetric bottle, and 0.45 mL water or pH=8.0 buffer was separately added. APL-1078 was completely dissolved, indicating its solubility was >100 mg/mL in both solvents. In a third test, 50 mg APL-1078 was added into 100 mL volumetric bottle, and 0.045 mL water or pH=8.0 buffer was separately added. APL-1078 was completely dissolved, indicating its solubility was >1000 mg/mL in all three solvents.

TABLE 2

Solubility of nitroxoline (APL-1202) and exemplary nitroxoline salts tested at different pHs ranging from pH 1.2 to pH 8.0.

| APL-Code | Solubility (mg/mL) | | | | | | | |
|---|---|---|---|---|---|---|---|---|
| | pH 1.2 | pH 4.5 | pH 5 | pH 6 | pH 6.8 | pH .4 | pH 8.0 | water |
| 1202 | <0.1 | <0.1 | <0.1 | <0.1 | <0.1 | <0.1 | <0.1 | <0.1 |
| 1071 | <0.1 | <0.1 | <0.1 | <0.1 | <0.1 | <0.1 | <0.1 | <0.1 |
| 1074 | 1-10 | <0.1 | <0.1 | <0.1 | <0.1 | <0.1 | <0.1 | <0.1 |
| 1075 | <0.1 | <0.1 | <0.1 | <0.1 | <0.1 | <0.1 | <0.1 | <0.1 |
| 1076 | 1-10 | <0.1 | <0.1 | <0.1 | <0.1 | <0.1 | <0.1 | <0.1 |
| 1072 | <0.1 | <0.1 | <0.1 | <0.1 | <0.1 | <0.1 | <0.1 | 1-10 |
| 1077 | <0.1 | <0.1 | <0.1 | <0.1 | <0.1 | <0.1 | 1-10 | 1-10 |
| 1073 | <0.1 | <0.1 | <0.1 | <0.1 | <0.1 | <0.1 | <0.1 | <0.1 |
| 1078 | 0.1-1.0 | <0.1 | <0.1 | <0.1 | 0.1-1.0 | <0.1 | >1000 | >1000 |
| 1079 | <0.1 | <0.1 | <0.1 | <0.1 | <0.1 | <0.1 | 30-100 | 10-30 |
| 1080 | <0.1 | <0.1 | <0.1 | <0.1 | <0.1 | <0.1 | <0.1 | <0.1 |
| 1081 | <0.1 | <0.1 | <0.1 | <0.1 | 0.1-1.0 | <0.1 | 1-10 | 0.1-1.0 |
| 1082 | 0.1-1.0 | <0.1 | <0.1 | <0.1 | 0.1-1.0 | <0.1 | 1-10 | <0.1 |
| 1088 | 1-10 | NT[1] | NT | NT | <0.1 | 1-10 | NT | 30-100 |
| 1089 | 1-10 | NT | NT | NT | <0.1 | 1-10 | NT | 30-100 |
| 1090 | 0.1-1.0 | NT | NT | NT | <0.1 | 0.1-1.0 | NT | 1-10 |
| 1091 | 1-10 | NT | NT | NT | <0.1 | 1-10 | NT | 30-100 |
| 1092 | 1-10 | NT | NT | NT | <0.1 | 30-100 | NT | 30-100 |
| 1093 | 1-10 | NT | NT | NT | <0.1 | 1-10 | NT | 1-10 |
| 1116 | 0.1-1.0 | NT | NT | NT | <0.1 | 30-100 | NT | 30-100 |
| 1117 | 0.1-1.0 | NT | NT | NT | <0.1 | 1-10 | NT | 1-10 |
| 1118 | 1-10 | NT | NT | NT | <0.1 | 30-100 | NT | 30-100 |

[1]NT: Not tested.

The results of the experiment, as shown in Table 2, demonstrate that nitroxoline (compound APL-1202) has poor solubility at all pHs tested (<0.1 mg/mL), i.e., from pH 1.2 to 8. Acid addition salts of nitroxoline, such as compounds APL-1071 (hydrochloride salt), APL-1074 (hydrobromide salt), APL-1075 (nitric acid salt), and APL-1076 (PhSO$_3$H salt) also showed poor solubility at all pHs tested (<0.1 mg/ml, with the exception of APL-1074 and APL~1076, which showed as solubility of 1-10 mg/mL at pH 1.2). In contrast, base addition salts, particularly those obtained by treating nitroxoline with a metal hydroxide, such as compounds APL-1072 (sodium salt) and APL-1077 (potassium salt), or an amine, such as APL-1078 (choline salt), APL-1079 (diethylamine salt), APL-1081 (piperazine salt), and APL-1082 (L-arginine), have significantly improved solubility at a physiologically relevant pH, i.e., pH of 4.5 to 8.

Accordingly, the solubility of particular nitroxoline salts is not necessarily predictable, which illustrates the surprising discovery of the present invention of base addition salts of nitroxoline having improved solubility in aqueous medium at a physiological pH.

Example 24

Measurement of In Vivo Urinary Excretion of Nitroxoline and Nitroxoline Salts in Beagle Dogs Each of three male beagle dogs with body weights ranging from 10-13 kg, were orally dosed with a tablet containing 75 mg nitroxoline after fasting overnight. Urine samples were collected in the following periods of time: 0-2, 2-4, 4-6, 6-8, 8-24 h. Urine samples were analyzed by LC/MS/MS method utilizing an Agilent 1100 HPLC system with a CTC auto-sampler, an AB API4000 mass spectrometer, and a column of ACQUITY UPLC BEH C18 (2.1*50 mm) Dexamethasone was used as an internal standard. The Nitroxoline peak was monitored with a targeted m/z=190.9 and a fragment of 144.7. The range of linearity was determined to be 25~5000 ng/mL. The amounts of nitroxoline observed in the urine samples at various period of time are summarized in Table 3.

TABLE 3

Amount of nitroxoline observed in urine samples from beagle dogs administered nitroxoline.

| Collection time (hr) | Mass (ng) | | | Mean (ng) | SD |
|---|---|---|---|---|---|
| | Dog #1 | Dog #2 | Dog #3 | | |
| 0-2 | 5670 | 60420 | 105600 | 57230 | 50041 |
| 2-4 | 0 | 13005 | 5502 | 9254 | NA |
| 4-6 | 0 | 817 | 28696 | 14757 | NA |
| 6-8 | 0 | 2582 | 5808 | 4195 | NA |
| 8-24 | 49680 | 5664 | 8282 | 21209 | 24692 |
| Total mass(ng) | 55350 | 82489 | 153888 | 97242 | 50899 |
| Body weight (g) | 11000 | 11650 | 11750 | 11467 | 407 |
| Dose (mg) | 75 | 75 | 75 | 75 | |
| *f (%) | 0.074 | 0.11 | 0.205 | 0.13 | 0.068 |

NA: Not available
*f(%): refers to percentage of total mass of excreted drug versus the dose amount The same study was repeated with APL-1092, nitroxoline lysine salt. Each dog was dosed with a tablet of 133 mg of APL-1092, which is equivalent to 75 mg of nitroxoline in terms of moles of nitroxoline. The amounts of nitroxoline in the urine samples at various period of time are summarized in Table 4.

TABLE 4

Amount of nitroxoline observed in urine samples of beagle dogs administered nitroxoline lysine salt.

| Collection time (hr) | Mass (ng) | | | Mean (ng) | SD |
|---|---|---|---|---|---|
| | Dog #1 | Dog #2 | Dog #3 | | |
| 0-2 | 0 | 15153 | 163020 | 89086 | NA |
| 2-4 | 0 | 130150 | 219300 | 174725 | NA |
| 4-6 | 0 | 96900 | 0 | 96900 | NA |
| 6-8 | 0 | 22165 | 0 | 22165 | NA |
| 8-24 | 825000 | 49575 | 329400 | 401325 | 392684 |
| Total mass (ng) | 825000 | 313943 | 711720 | 616888 | 268402 |
| Body Weight (g) | 11600 | 12900 | 10500 | 11667 | 1201 |
| Dose (mg) | 75 | 75 | 75 | 75 | |
| *f (%) | 1.1 | 0.419 | 0.949 | 0.823 | 0.358 |

NA: Not available
*f(%): refers to percentage of total mass of excreted drug versus the dose amount Example 25

Measurement of In Vivo Urinary Excretion of Nitroxoline and Nitroxoline Salts in Mice Each of six male CD-1 ICR mice, with body weights ranging from 15-20 g, were orally dosed with nitroxoline at a dose of 41.8 mg/Kg after fasting overnight. Urine samples were collected in the following periods of time: 0-2, 2-6, 6-24 h. Due to the small volume of the urine from mice, the collecting system in the cage was washed with water at each collecting time. Urine samples and their wash samples were analyzed according to the same methods used in the beagle dog study (Example 24). The amounts of nitroxoline observed in the urine samples of the mice at various period of time are summarized in Table 5.

TABLE 5

Amount of nitroxoline observed in urine samples from mice administered nitroxoline

| Collection time (hr) | Mass (ng) | | | | | | | |
|---|---|---|---|---|---|---|---|---|
| | Mice #9 | Mice #10 | Mice #11 | Mice #12 | Mice #13 | Mice #14 | Mean (ng) | SD |
| 0-2 | 109552 | 10584 | 1360 | 21035 | 61040 | 137700 | 56879 | 56275 |
| 0~2 wash | 2856 | 6652.8 | 784 | 4212 | 8250 | 2352 | 4184 | 2804 |
| 2-6 | 10404 | 26418 | 17600 | 11412 | 14715 | 11000 | 15258 | 6112 |
| 2~6 wash | 1283 | 5325 | 957 | 2904 | 1530 | 346 | 2057 | 1812 |
| 6-24 | 47.8 | 109 | 50.9 | 81 | 1500 | 71.5 | 310 | 583 |
| 6~24 wash | 249 | 1428 | 2341 | 1558 | 1102 | 152 | 1138 | 833 |
| Total mass (ng) | 124391 | 50517 | 23093 | 41201 | 88137 | 151622 | 79827 | 50555 |
| Body wt. (g) | 0.0196 | 0.0196 | 0.0188 | 0.0188 | 0.0194 | 0.0186 | 0.019 | 0 |
| Dose (mg) | 0.819 | 0.819 | 0.786 | 0.786 | 0.811 | 0.777 | 0.8 | 0.019 |
| *f (%) | 15.2 | 6.17 | 2.94 | 5.24 | 10.9 | 19.5 | 10 | 6.4 |

*f (%): refers to percentage of total mass of excreted drug versus the dose amount The same study was repeated with APL-1092, nitroxoline lysine salt. Each mouse was dosed with APL-1092 at a dose of 77.7 mg/kg, which is equivalent to 41.8 mg/Kg of nitroxoline in terms of moles of nitroxoline. The amounts of nitroxoline in the urine and wash samples at various period of time are summarized in Table 6.

TABLE 6

Amount of nitroxoline observed in urine samples from mice administered nitroxoline lysine salt.

| Collection time (hr) | Mass (ng) | | | | | | | |
|---|---|---|---|---|---|---|---|---|
| | Mice #15 | Mice #16 | Mice #17 | Mice #18 | Mice #19 | Mice #20 | Mean (ng) | SD |
| 0-2 | 51600 | 84300 | 31970 | 107380 | 31122 | 120000 | 71062 | 38448 |
| 0~2 wash | 113000 | 25240 | 15015 | 25300 | 47650 | 19320 | 40921 | 37063 |
| 2-6 | 3308.5 | 5263.2 | 1084 | 17458 | 3500 | 1846 | 5410 | 6077 |
| 2~6 wash | 6055 | 3618 | 8190 | 4635 | 4868 | 1960 | 4888 | 2122 |
| 6-24 | 37.5 | 101.64 | 10.4 | 51 | 73 | 79.6 | 58.8 | 33 |
| 6~24 wash | 296 | 158 | 246 | 286 | 227 | 190 | 234 | 53.9 |
| Total mass | 174297 | 118681 | 56516 | 155110 | 87439 | 143396 | 122573 | 44228 |
| Body wt. (kg) | 0.0136 | 0.0144 | 0.0138 | 0.0148 | 0.0134 | 0.0196 | 0.015 | 0.002 |
| Dose (mg) | 0.502 | 0.531 | 0.509 | 0.546 | 0.494 | 0.723 | 0.551 | 0.087 |
| *f (%) | 34.7 | 22.3 | 11.1 | 28.4 | 17.7 | 19.8 | 22.3 | 8.3 |

*f (%): refers to percentage of total mass of excreted drug versus the dose amount More surprisingly, the results of the experiments of Examples 24 and 25 indicate that nitroxoline base addition salts according to the invention, and particularly nitroxoline lysine salt, demonstrated in vivo increased urine excretion when compared to nitroxoline itself. As shown in Table 7, which summarizes the results shown in Tables 5 and 6, after nitroxoline lysine salt was dosed at the equivalent amount of nitroxoline in terms of moles, nitroxoline lysine salt showed an increase in drug excretion in the urine of beagle dogs of more than five times as compared to that of nitroxoline. In mice, nitroxoline lysine salt also showed an increase of drug excretion in the urine, although the degree of the increase was approximately two times greater than than of nitroxoline.

TABLE 7

Comparison of excretion of nitroxoline and nitroxoline lysine salt in beagle dogs and mice.

| | In Dogs* | | In Mice** | |
|---|---|---|---|---|
| | APL-1202 | APL-1092 | APL-1202 | APL-1092 |
| 24-Hr Accumulated drug in the urine (μg) | 97 ± 51 | 617 ± 268 | 79.8 ± 50.6 | 139 ± 50 |
| Ratio of doses excreted through urine F (%) | 0.130 ± 0.068 | 0.823 ± 0.358 | 10.0 ± 0.4 | 22.3 ± 8.3 |

*In dogs, APL-1202 was dosed with 75 mg, APL-1092 was dosed with an equivalent amount of 75 mg of APL-1202;
**In mice, APL-1202 was dosed at 41.8 mg/Kg, APL-1092 was dosed with an equivalent dose of 41.8 mg/Kg of APL-1202.

REFERENCES

1. Shim J S, Matsui Y, Bhat S, Nacev B A, Xu J, Bhang H E, Dhara S, Han K C, Chong C R, Pomper M G, So A, Liu J O. Effect of nitroxoline on angiogenesis and growth of human bladder cancer. J Natl Cancer Inst. 2010; 102(24): 1855-73. Erratum in: J Natl Cancer Inst. 2011; 103(13): 1070.
2. Mirković B, Renko M, Turk S, Sosič I, Jevnikar Z, Obermajer N, Turk D, Gobec S, Kos J. Novel mechanism of cathepsin B inhibition by antibiotic nitroxoline and related compounds. ChemMedChem. 2011; 6(8):1351-6
3. Jiang H, Taggart J E, Zhang X, Benbrook D M, Lind S E, Ding W Q. Nitroxoline (8-hydroxy-5-nitroquinoline) is more a potent anti-cancer agent than clioquinol (5-chloro-7-iodo-8-quinoline). Cancer Lett. 2011; 312(1):11-7.
4. Bergogne-Berezin E, Berthelot G, Muller-Serieys C. Present status of nitroxoline Pathol Biol (Paris). 1987; 35 (5 Pt 2):873-8.
5. Yatsenko A V, Paseshnichenko K A, Chernysheva V V and Schenkb H Powder diffraction study of the hydrogen bonds in nitroxoline and its hydrochloride Acta Cryst. 2002; C58: 19-21.
6. Gao G Y, Lin S Y Thermodynamic Investigations of Nitroxoline Sublimation by Simultaneous DSC-FTIR Method and Isothermal TG Analysis J. Pharm. Sciences 2009: 1-7.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A base addition salt of nitroxoline, wherein the salt is an ammonium salt, amine salt, or quaternary ammonium salt.

2. An amine salt of nitroxoline or a quaternary ammonium salt of nitroxoline,
   wherein the amine is a substituted or unsubstituted alkylamine selected from the group consisting of diethylamine, 2-diethylaminoethanol, N,N-dimethylethanolamine, tromethamine, ethanolamine, and diolamine; a heterocyclic amine selected from the group consisting of piperazine, substituted pyrrolidine, 1-(2-hydroxyethyl)-pyrrolidine, and 4-(2-hydroxyethyl)-morpholine; a basic amino acid selected from the group consisting of arginine and lysine; N-methylglucamine; or ethylenediamine; and
   wherein the quaternary ammonium is choline.

3. The salt of claim 2, being the quaternary ammonium salt of nitroxoline, wherein the quaternary ammonium is choline.

4. The salt of claim 1, wherein the amine is selected from the group consisting of alkylamines, heterocyclic amines, basic amino acids, amino sugars, and polyamines.

5. The salt of claim 1, wherein the salt is obtained by mixing nitroxoline and a base selected from the group consisting of amines, quaternary ammonium hydroxides, and ammonium hydroxide in one or more solvents selected from the group consisting of acetone, methyl-isobutylketone, dichloromethane, toluene, pyridine, isobutyronitrile, acetonitrile, tetrahydrofuran, methanol, ethanol, and isopropanol.

6. The salt of claim 1, wherein the salt has a solubility of at least 0.1 mg/mL in water or an aqueous medium having a pH between 4.5 and 8.0.

7. A method of preparing the base addition salt of nitroxoline of claim 1, the method comprising:
   (i) mixing nitroxoline and an amine base, ammonium hydroxide, or a quaternary ammonium hydroxide in an organic solvent to obtain the base addition salt of nitroxoline; and
   (ii) recovering the base addition salt of nitroxoline from the organic solvent.

8. The method according to claim 7, wherein the organic solvent comprises one or more solvents selected from the group consisting of acetone, methyl-isobutylketone, dichloromethane, toluene, pyridine, isobutyronitrile, acetonitrile, tetrahydrofuran, methanol, ethanol, and isopropanol.

9. The method according to claim 7, wherein the recovery step comprises crystallizing the base addition salt of nitroxoline from the organic solvent.

10. A crystal of nitroxoline choline salt, wherein the crystal has peaks at the diffraction angles (2θ) with an exactness of ±0.2θ: 9.96, 12.12, 17.72, and 20.08 in its powder X-ray diffraction pattern.

11. A pharmaceutical composition comprising a therapeutically effective amount of the base addition salt of nitroxoline according to claim 4 and one or more pharmaceutically acceptable carriers.

12. The pharmaceutical composition of claim 11, wherein the pharmaceutical composition is a sustained-release composition, a composition formulated for injectable administration, or a liquid composition.

13. A method of preparing the pharmaceutical composition according to claim 11 comprising combining the therapeutically effective amount of the base addition salt of nitroxoline and the one or more pharmaceutically acceptable carriers.

14. A method of treating a disease, disorder or condition in a subject in need thereof, the method comprising administering to the subject a pharmaceutical composition according to claim 11, wherein the disease, disorder, or condition is selected from the group consisting of a urinary tract infection, bladder cancer, renal cancer, and prostate cancer.

15. A method of providing a protective urinary effect in a subject in need thereof, the method comprising administering to the subject a pharmaceutical composition according to claim 11.

16. The salt of claim 2, being the amine salt of nitroxoline, wherein the amine is lysine.

17. The salt of claim 2, being the amine salt of nitroxoline, wherein the amine is arginine.

18. A pharmaceutical composition comprising a therapeutically effective amount of the amine salt of nitroxoline or quaternary ammonium salt of nitroxoline according to claim 2 and one or more pharmaceutically acceptable carriers.

19. A method of treating a disease, disorder or condition in a subject in need thereof, the method comprising administering to the subject a pharmaceutical composition according to claim 18, wherein the disease, disorder, or condition is selected from the group consisting of a urinary tract infection, bladder cancer, renal cancer, and prostate cancer.

20. A method of providing a protective urinary effect in a subject in need thereof, the method comprising administering to the subject a pharmaceutical composition according to claim 18.

* * * * *